(12) United States Patent
Chavan

(10) Patent No.: US 12,285,163 B2
(45) Date of Patent: Apr. 29, 2025

(54) KNOTLESS ORTHOPEDIC STABILIZATION SYSTEM

(71) Applicant: Dunamis Medical Technologies, LLC, Greenville, AL (US)

(72) Inventor: Prithviraj Chavan, Greenville, AL (US)

(73) Assignee: Dunamis Medical Technologies, LLC, Greenville, AL (US)

( * ) Notice: Subject to any disclaimer, the term of this patent is extended or adjusted under 35 U.S.C. 154(b) by 134 days.

(21) Appl. No.: 17/954,753

(22) Filed: Sep. 28, 2022

(65) Prior Publication Data
US 2023/0020174 A1 Jan. 19, 2023

Related U.S. Application Data

(63) Continuation of application No. 16/816,440, filed on Mar. 12, 2020, now abandoned.
(Continued)

(51) Int. Cl.
*A61B 17/04* (2006.01)
*A61B 17/06* (2006.01)
(Continued)

(52) U.S. Cl.
CPC .... *A61B 17/0487* (2013.01); *A61B 17/06166* (2013.01); *A61B 17/683* (2013.01);
(Continued)

(58) Field of Classification Search
CPC ............ A61B 17/0401; A61B 17/0404; A61B 17/0459; A61B 17/0466
See application file for complete search history.

(56) References Cited

U.S. PATENT DOCUMENTS 5,306,290 A * 4/1994 Martins .............. A61B 17/0401
606/232
6,027,523 A * 2/2000 Schmieding ....... A61B 17/0401
606/232
(Continued)

FOREIGN PATENT DOCUMENTS

WO 2016049538 3/2016

OTHER PUBLICATIONS

Extended European Search Report 18761711.3 dated Mar. 11, 2021.
(Continued)

*Primary Examiner* — Nicholas W Woodall
(74) *Attorney, Agent, or Firm* — Jay B. Bell, Esq.

(57) ABSTRACT

Embodiments of knotless button-suture assemblies for orthopedic stabilization are disclosed. The button-suture assembly includes a button having a first opening, a second opening and a center opening. The assembly further includes a tensioning member having two tensioning member ends exiting from the first opening and the second opening of the button and disposed in the proximal direction. The assembly further includes a locking pin mated with the button through the center opening of the button in such a manner that allows a proximal movement of the tensioning member when a pulling force is applied to the tensioning member ends towards a proximal direction and prevents a distal movement of the tensioning member when the pulling force applied to the loose ends of the tensioning member ceases to exist.

12 Claims, 23 Drawing Sheets

Related U.S. Application Data

(60) Provisional application No. 62/817,313, filed on Mar. 12, 2019.

(51) Int. Cl.
    *A61B 17/68*         (2006.01)
    *A61B 17/82*         (2006.01)
    *A61B 17/84*         (2006.01)

(52) U.S. Cl.
    CPC ...... *A61B 17/82* (2013.01); *A61B 2017/0404* (2013.01); *A61B 2017/0414* (2013.01); *A61B 2017/0453* (2013.01); *A61B 2017/0496* (2013.01)

(56) References Cited

U.S. PATENT DOCUMENTS

| | | | |
|---|---|---|---|
| 6,086,608 A * | 7/2000 | Ek | A61B 17/0487 606/301 |
| 9,192,368 B2 * | 11/2015 | Perriello | A61B 17/0401 |
| 10,499,900 B2 * | 12/2019 | Wade | A61B 17/0401 |
| 11,109,855 B2 | 9/2021 | Shoshtaev et al. | |
| 11,812,946 B2 | 11/2023 | Shoshtaev et al. | |
| 2007/0162125 A1 | 7/2007 | Lebeau et al. | |
| 2012/0065731 A1 | 3/2012 | Justin | |
| 2012/0150297 A1 | 6/2012 | Denham et al. | |
| 2013/0035720 A1 | 2/2013 | Perriello et al. | |
| 2013/0103081 A1 * | 4/2013 | Wolf | A61B 17/0401 606/232 |
| 2013/0158600 A1 | 6/2013 | Conklin et al. | |
| 2013/0268073 A1 | 10/2013 | Albertorio et al. | |
| 2016/0220347 A1 | 8/2016 | Hoover et al. | |

OTHER PUBLICATIONS

PCT International Search Report and Written Opinion of the International Searching Authority, PCT/US2018/020506 dated Jun. 20, 2018.

* cited by examiner

KNOTLESS ORTHOPEDIC STABILIZATION SYSTEM

CROSS-REFERENCES TO RELATED APPLICATIONS

The present application is continuation of U.S. patent application Ser. No. 16/816,440, filed Mar. 12, 2020, and entitled "Knotless Orthopedic Stabilization System," which claims the benefit of priority under 35 U.S.C. § 119(e) to U.S. Provisional Application Ser. No. 62/817,313, filed on Mar. 12, 2019, which is incorporated herein by reference in its entirety.

FIELD

The present invention is generally directed toward a device and a method for use in a surgical repair of bone or tissue. More particularly, the present invention relates to the stabilization or repair of two or more bones or tissue fragments in orthopedic procedures.

BACKGROUND

Bone suspension devices, such as button-suture assemblies, that stabilize bone and tissue are known in the art. The current devices secure the bone by locking the suture or other tensioning member in place via a knot. In these procedures, after a hole is drilled through the bone, tensioning members are passed through it and fixated on the distal side of the hole. The bones are then pulled closer together and a knot is tied on the proximal side of the assembly to hold the tension. Tying a knot to hold the tensioning member tight is relatively difficult and can result in some of the tension being lost as the knot is completed and the tying mechanisms (whether tool or fingers) release their grip on the tensioning member. As a result, the loop of the knot springs back or relaxes one or more millimeters before the assembly is secured, and then resulting tension is significantly less than the tension initially intended.

Knotless systems exist that employ various mechanisms for length adjustment and locking. In most of these, either the strength of the construct (measured by tension to failure) or its stability (by way of loss of tension) are sacrificed in favor of attaining better ease of use.

SUMMARY

Assemblies that secure bone and tissue fragments lose tension before the assemblies can lock resulting in inefficient placement of the assembly during surgical procedures. The presently disclosed invention provides for an orthopedic stabilization device and button-suture assembly that includes suture or tensioning members on one end and a locking pin mated with a button on the other to allow tensioning and to cause an automatic locking when the applied tension is released or ceases to exist. The disclosed invention provides a mechanism that utilizes the (construct) tension generated during the tensioning step to securely lock the construct during the locking step. The locking is achieved by means of one or more pinch points designed to maximize the tensile strength of the construct by increasing the surface area of contact between the tensioning member and the locking elements (e.g., locking pin) and decreasing the stress that the tensioning member is exposed to in a locked state.

Embodiments of an orthopedic stabilization device are disclosed. In an embodiment, the orthopedic stabilization device includes a button having a plurality of openings and a locking pin having a proximal end and a distal end. The locking pin is configured to mate with the button through a center opening in the button. The orthopedic stabilization device further includes a tensioning member having two tensioning member ends passing through a first opening and a second opening in the button and disposed outwardly towards a proximal direction of the button. The tensioning member forms one or more tensioning member loops by at least passing through a transverse opening in a distal member of the locking pin.

BRIEF DESCRIPTION OF THE DRAWINGS

Further advantages of the invention will become apparent by reference to the detailed description of preferred embodiments when considered in conjunction with the drawings:

FIG. 7A depicts a cross sectional view of the button-suture assembly being tensioned. FIG. 7B depicts a cross sectional view of the suspension device in locked position.

FIG. 8A depicts a cross sectional view of the locking pin being removed from the button. FIG. 8B depicts a cross sectional view of the button-suture assembly in unlocked position.

FIG. 12A depicts a perspective view of the button-suture assembly with footprint extender. FIG. 12B depicts a perspective view of the button-suture assembly with footprint extender. FIG. 12C depicts a perspective view of the button being pulled through the footprint extender. FIG. 12D depicts a cross sectional view of the button inside the footprint extender.

FIG. 13A depicts a perspective view of the button-suture assembly in an unlocked state. FIG. 13B depicts a sectional view of the button-suture assembly in a locked state.

DETAILED DESCRIPTION OF A PREFERRED EMBODIMENT

Figure 1:
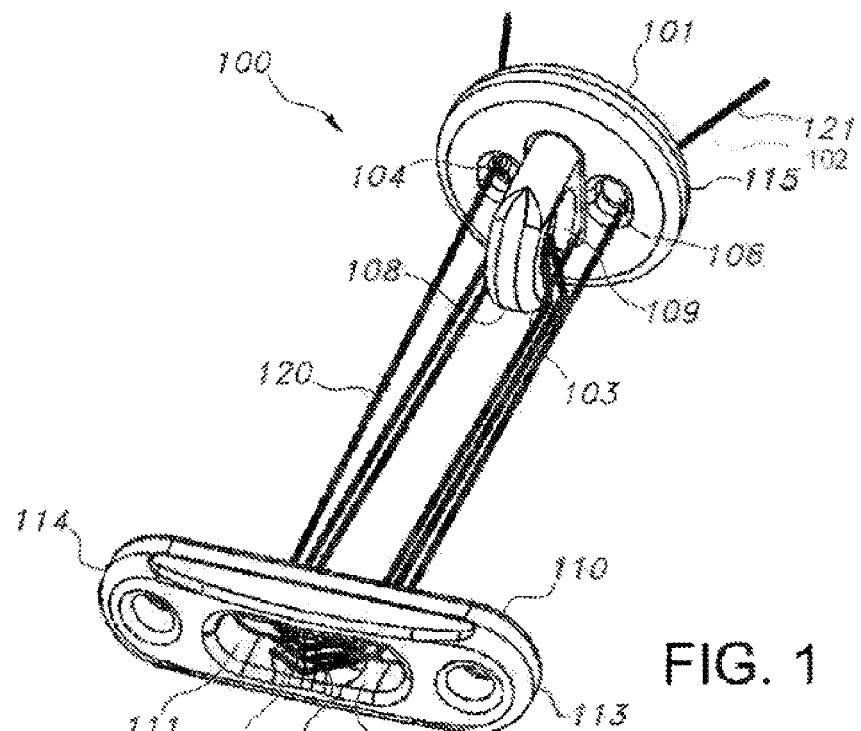
FIG. 1 depicts the preferred embodiment of a button-suture assembly.

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Conventional knotted button-suture assemblies lose tension after the knot is tied on the proximal side of the assembly during surgical procedures. Tying a knot in the tensioning members during surgery can be substantially difficult and, as previously described, may result in loss of tension after the knot is tied as it is released by the tying implements. This loss in tension allows the loop to relax or spring back at least one or more millimeters making the placement of the assembly during the surgical procedure less precise. Such loss in tension is therefore undesirable and needs to be minimized or prevented.

Disclosed knotless button-suture assembly is used for knotless stabilization of two or more tissue, bone or other body members. While the preferred embodiments are contemplated for the stabilization of two bone or tissue fragments, the disclosed button-suture assembly is versatile and can be used for a variety of different applications without departing from the scope of the ongoing description.

In an embodiment, the button-suture assembly includes a button having a first opening, a second opening and a center opening. The button-suture assembly includes a tensioning member having two tensioning member ends exiting from the first opening and the second opening of the button and disposed in the proximal direction. The button-suture assembly further includes a locking pin mated with the button through the center opening of the button in such a manner that allows a proximal movement of the tensioning member when a pulling force is applied to the tensioning member ends towards a proximal direction. Furthermore, a distal movement of the tensioning member is prevented when the pulling force applied to the ends of the tensioning member ceases to exist. Therefore, an automatic self-locking mechanism is provided that facilitates precise placement of the assembly during surgical procedures.

The locking pin includes a proximal member and a distal member. The distal member has a transverse opening. The knotless button-suture assembly further includes a baseplate having a plurality of holes. The tensioning member passes through two of the plurality of holes and the transverse opening in the distal member of the locking pin to form one or more tensioning member loops. The locking pin translates in a proximal direction relative to the button when the pulling force is applied to the two tensioning member ends towards the proximal direction. Additionally, the locking pin translates in a distal direction relative to the button when the pulling force ceases to exist subsequent to the applying of the pulling force to the two tensioning member ends towards the proximal direction.

In an embodiment, the locking pin has two indentations located on the proximal member of the locking pin disposed along the first opening and the second opening respectively to create two corresponding passages between the locking pin and an interior surface of the circumference of the button for the tensioning member to pass through. The locking pin mated with the button creates one or more pinch points in the two passages when the pulling force ceases to exist after the applying of the pulling force to the tensioning member ends. The one or more pinch points provide the retaining mechanism to prevent the slackness or relaxing of tension when the pulling force is released or removed. The tensioning member corresponds to one of: a careless suture, a suture with a jacket and a central core, and a tape. In an embodiment, the tensioning member has a length that lies in the range of around 250 mm to around 750 mm.

In certain implementations, the button-suture assembly is contemplated to be used as an orthopedic stabilization device. Embodiments of orthopedic stabilization device for stabilizing or repairing of two or more bones or tissue fragments. The orthopedic stabilization device includes a button having a plurality of openings. The stabilization device further includes a locking pin having a proximal end and a distal end. As will be described below, the locking pin is configured to mate with the button through a center opening in the button. The orthopedic stabilization device further includes a tensioning member having two tensioning member ends passing through a first opening and a second opening in the button. The tensioning member ends are disposed outwardly towards a proximal direction of the button. The tensioning member forms one or more tensioning member loops by at least passing through a transverse opening in a distal member of the locking pin. The orthopedic stabilization device further includes a baseplate having a plurality of holes. In an embodiment, the tensioning member passes through two of the plurality of holes and the transverse opening in the distal member of the locking pin to form the one or more tensioning member loops.

In an embodiment, the locking pin translates in a proximal direction relative to the button when a pulling force is applied to the two tensioning member ends towards the proximal direction. Furthermore, the locking pin translates in a distal direction relative to the button when the pulling force ceases to exist subsequent to the applying of the pulling force to the two tensioning member ends towards the proximal direction.

In an embodiment, the locking pin includes two indentations located on the proximal end of the locking pin disposed along the first opening and the second opening respectively to create two corresponding passages between the locking pin and an interior surface of the circumference of the button for the tensioning member to pass through. The passages allow a proximal movement of tensioning member when a pulling force is applied to the tensioning member ends towards the proximal direction. The passages prevent a distal movement of tensioning member when the pulling force ceases to exist after the applying of the pulling force to the tensioning member.

The proximal end of the locking pin has a cross sectional dimension greater than the center opening and the distal end of the locking pin has a cross sectional dimension similar to the center opening. The tensioning member is manufactured from a material selected from a group comprising of polymer filaments, metallic filaments, organic filaments, carbon fiber and carbon nanotubes. In an embodiment, the tensioning member has a length that lies in the range of around 150 mm to around 1000 mm. In yet another embodiment, the inner circumference of the locking pin is threaded. In an embodiment, the button has one or more tool access cuts on the exterior proximal surface.

In an embodiment, the orthopedic stabilization device further includes an anchor having one or more keyholes. In such an embodiment, the tensioning member passes through the one or more keyholes of the anchor and the transverse opening in the distal member of the locking pin to form the one or more tensioning member loops. In certain other embodiments, the anchor has a threaded region on the outer circumference or lateral surface and a pointed tip at a distal end.

In an embodiment, the orthopedic stabilization device further includes a baseplate secured inside the anchor and disposed in a direction transverse to the length of the anchor. The anchor has a vertical slot along the length of the anchor. In such an embodiment, the tensioning member passes through the vertical slot and through two of the plurality of holes in the baseplate and the transverse opening in the distal member of the locking pin to form the one or more tensioning member loops.

In an embodiment, the anchor has a vertical slot along the length of the anchor and a horizontal bridge towards the distal end of the anchor. In such an embodiment, the tensioning member passes through the vertical slot and around the bridge and through the transverse opening in the distal member of the locking pin to form the one or more tensioning member loops. The anchor is made from a material selected from a group comprising of PEEK, polymer, metal, fiber material, polymer composite and the like. Furthermore, the anchor has an anchor component at its proximal end configured to lock the tensioning member.

In an embodiment, the orthopedic stabilization device further includes a screw having an interior channel. In such an embodiment, the tensioning member passes through the interior channel and transverse opening in the distal member of the locking pin to form the one or more tensioning member loops.

In an embodiment, the orthopedic stabilization device further includes a baseplate having a plurality of holes, disposed towards the distal end of the screw. In such an embodiment, the tensioning member passes through the interior channel of the screw and through two of the plurality of holes in the baseplate and also the transverse opening in the distal member of the locking pin to form the one or more tensioning member loops.

In an embodiment, the orthopedic stabilization device further includes an anchor having a center hole. The tensioning member passes through the center hole of the anchor and the transverse opening in the distal member of the locking pin to form the one or more tensioning member loops.

It is to be understood that one or more tensioning member loops can be formed using various components, such as, but not limited to a baseplate, a screw, an anchor, a tape, a button with plurality of holes, a locking pin with various configurations and dimensions, a secondary loop, a plate with indentations, bridges, etc. without departing from the scope of the ongoing description. The one or more tensioning member loops serve the purpose of retaining the tension (resulting from tensioning step) once the assembly self-locks itself. The ongoing description might have excluded many ways and means to form tensioning member loops for the sake of brevity but any such ways and means can be implemented for the purposes of the ongoing description.

FIGS. 1-4 depict various embodiments of the button-suture assembly 100. As shown, the button-suture assembly 100 includes a suspension device 115, a baseplate 110, and a tensioning member 102. The tensioning member 102 can be a coreless suture, a suture with a jacket and a central core, or a tape. The tensioning member 102 has two loose tensioning member ends (e.g. 121) disposed outwardly towards a proximal direction of the suspension device 115.

Figure 5:
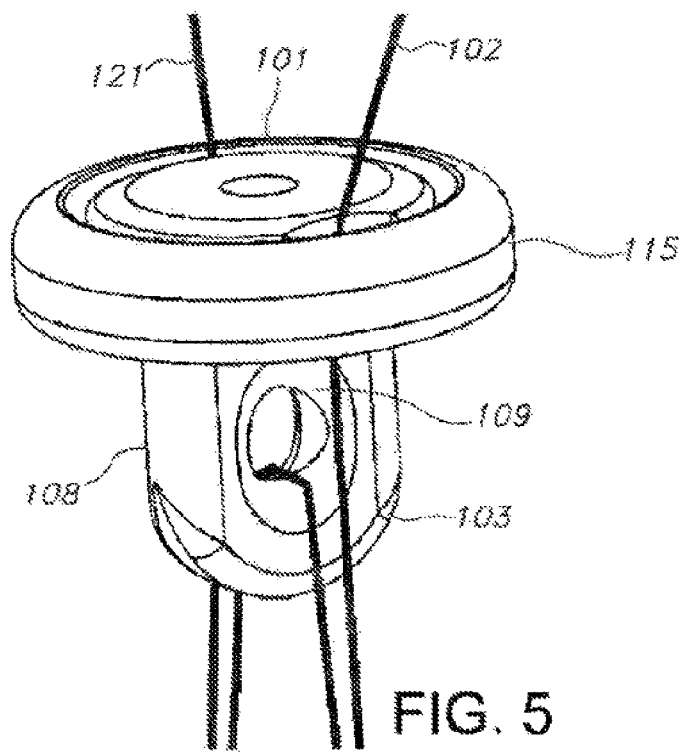
FIG. 5 depicts a perspective view of a locking pin of the button-suture assembly.

The suspension device 115 is further comprised of a button 101 and a locking pin 103 (as shown in FIG. 5). The button 101 is preferably round with three openings: a first opening 104, a center opening 105, and a second opening 106. The first opening 104 is configured to mate with the tensioning member 102 and the second opening 106 is configured to mate with the tensioning member 102 located on either side of the center opening 105. It may be noted that the tensioning member 102 follows a path through the button-suture assembly 100 that begins with the loose tensioning member ends 121. The tensioning member ends 121 exit outwardly from the first and second openings (104, 106). The tensioning member 102 extends through the first and second openings (104, 106) towards a distal direction with respect to the suspension device 115 to loop through holes or openings in various embodiments.

Tensioning member 102 is contemplated as being manufactured out of a variety of fibers or filaments including but not limited to polymer filaments (e.g., EMWPE, UEMWPE, PET, PTFE, PEEK, PEKK, PLA, PLLA, etc.), metallic filaments (e.g., Nitinol, Titanium, Titanium alloys, Tantalum, Stainless Steel, etc.) or organic filaments (e.g., Collagen, Silk, etc.) or other filaments such as carbon fiber or carbon nanotubes, etc. Tensioning member 102 is further contemplated to correspond to, but not limited to, a coreless suture, a suture with a jacket and a central core, a tape or any other tension member available or contemplated. The length of the tensioning member 102 is contemplated as being between around 150 mm and around 1000 mm in length and more preferably between around 300 mm and around 1000 mm in length and most preferably between around 250 mm and around 750 mm in length. To prevent glove tears, surgeons can use hemostat forceps to roll the tensioning member 102 during a procedure utilizing the button suture assembly 100.

Figure 6:
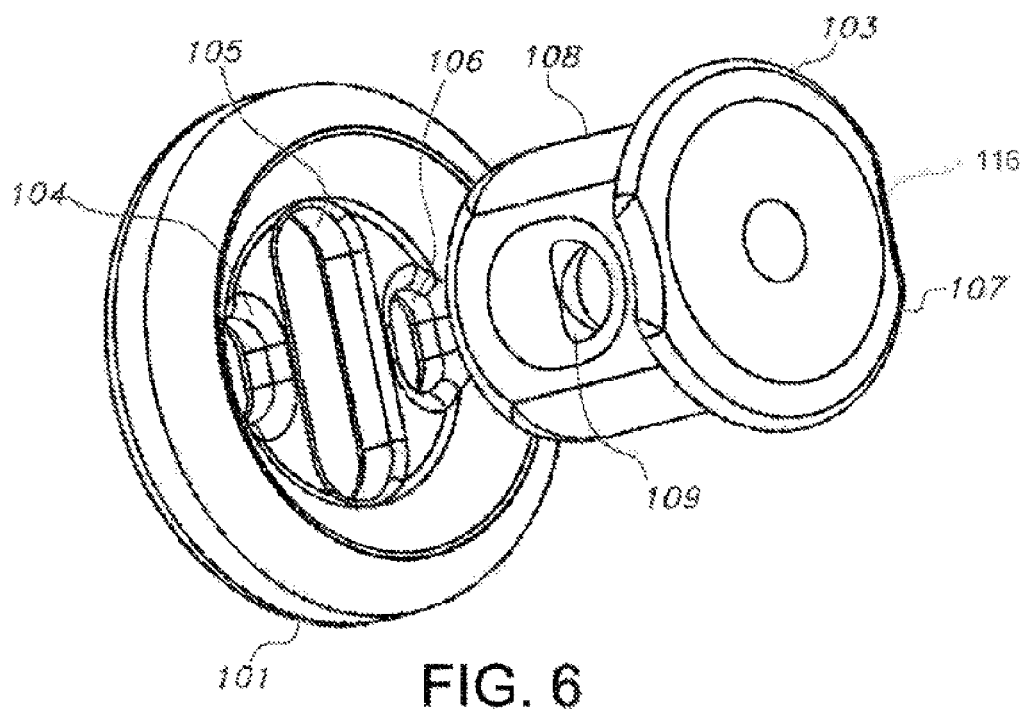
FIG. 6 depicts a perspective view of the button and locking pin of the button-suture assembly.

The center opening 105 is large enough to accept a distal member 108 of the locking pin 103. Accordingly, the locking pin 103 mates with the center opening 105 of the button 101 and includes a retaining mechanism configured to allow the tensioning member 102 to pass through one or more indented portions or indentations 116 (as shown in FIG. 6) of the locking pin 103. Such indented portions are positioned against the interior surface 117 of the circumference of the button 101 when and preferably, only when tension is applied to the loose tensioning member ends 121. It should be understood that the indentations 116 are optional and generally serve the purpose of compensating for the thickness of the tensioning member 102 and allowing the locking pin 103 to sit closer to the button 101 thereby reducing the prominence of the suspension device 115 above the bone (as shown in an embodiment in FIG. 7A). In an embodiment, the indentations 116 may also serve the purpose of constraining the side-to-side or rotational (excepting the twisting of the tensioning member along its long axis) motion of the tensioning member 102 with the suspension device 115. The portion of the tensioning member 102 extending from the suspension device 115 to the baseplate 110 is referred to as the double tensioning member loop 120 as shown in FIG. 1-FIG. 4.

In an embodiment, the indentations 116 of the locking pin 103 are located on opposite sides of the proximal end 107 of the locking pin 103 as shown in FIG. 5 & FIG. 6. The proximal end 107 has a cross-sectional dimension greater than the center opening 105 of the button 101 to prevent the locking pin 103 from sliding out of the center opening 105. Each indentation 116 creates a passage 118 for the tensioning member 102 between the locking pin 103 and button 101 thereby creating one or more pinch points 119. The indentations 116 have large surface area with rounded edges and flattened conical surfaces to preferably maximize the contact surface area between the tensioning member 102 and the suspension device 115. The distal member 108 of the locking pin 103 contains a transverse opening 109 through which the tensioning member 102 can pass. In an embodiment, the tensioning member 102 forms one or more tensioning member loops (e.g., 124, 125, 126, 132) by at least passing through the transverse opening 109 in the distal member 108 of the locking pin 103.

Figure 7A:
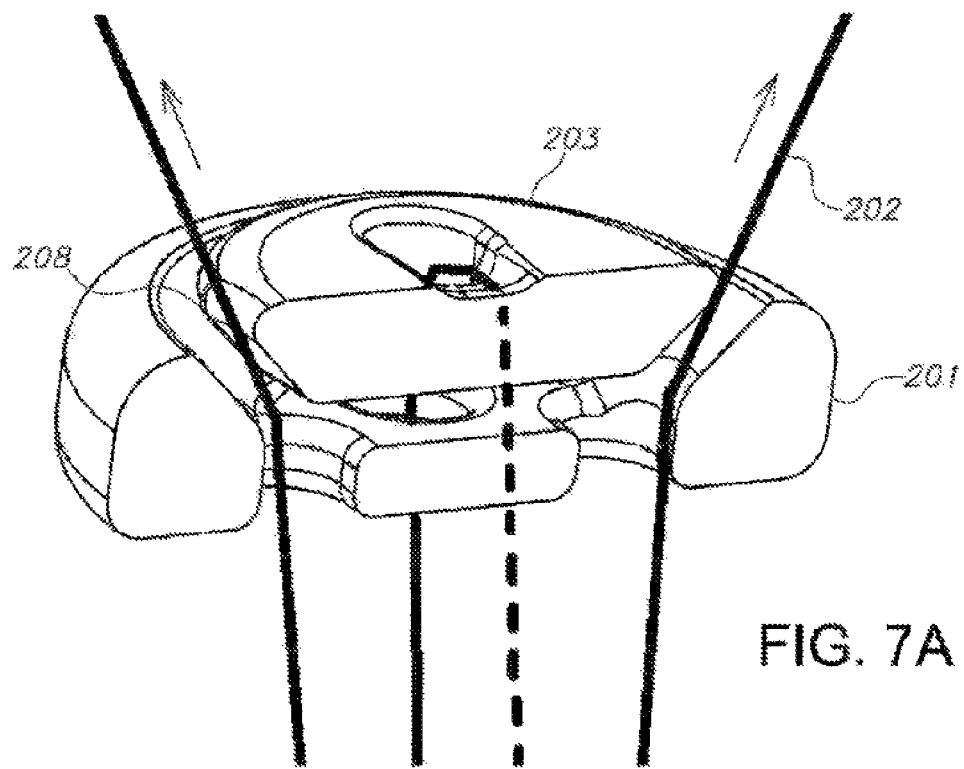
FIGS. 7A-7B depict the locking mechanism of a suspension device of the button-suture assembly. Individually.
Figure 9:
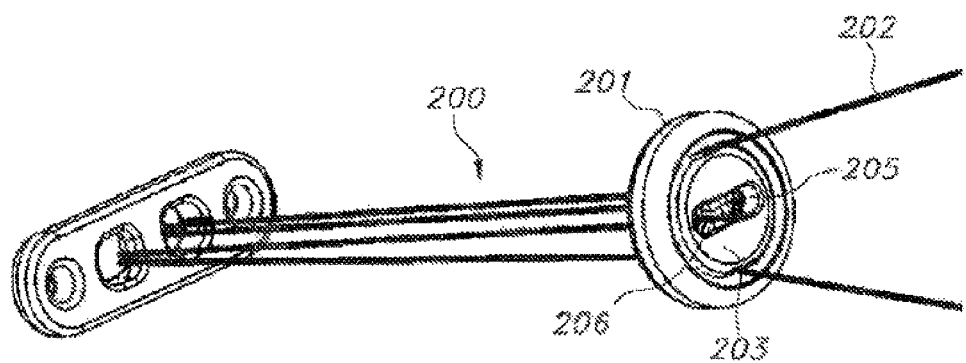
FIG. 9 depicts yet another perspective view of an embodiment of the button-suture assembly without a locking pin.
Figure 10:
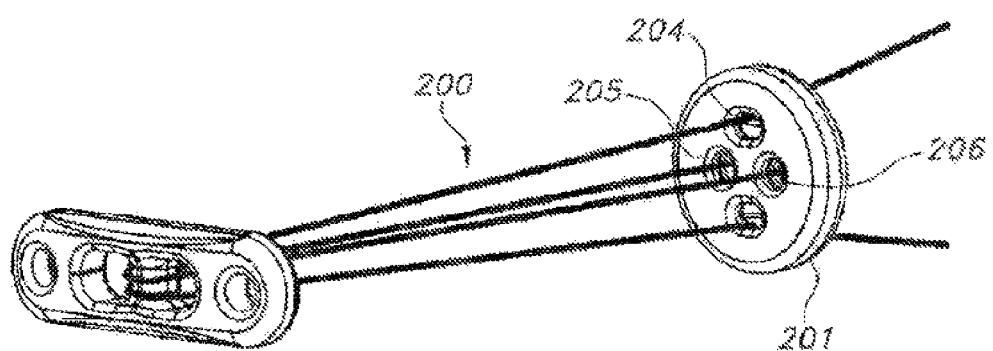
FIG. 10 depicts another perspective view of an embodiment of the button-suture assembly without a locking pin.

In an embodiment, the suspension device 115 includes a locking pin 203 (as shown in FIG. 7A) that has a proximal member and no distal member. In such an embodiment, the locking pin 203 has two through holes (as shown in FIG. 9 and FIG. 10). Furthermore, the button 201 has four openings. The first and second openings (204) mate with the two loose tensioning member ends and the third and fourth openings (205 and 206) of the button 201 coincide with the through holes of the locking pin 203 respectively. Furthermore, the cross-sectional dimension of the proximal surface of the button 201 is greater than the locking pin 203 to accommodate the locking pin 203 without prominently protruding when in a mating arrangement. The locking pin 203 has indentations (e.g., 116) that rests against the inner surface 208 of the button. The tensioning member 202 passes through the first and second openings (204) of the button 201 and also through the third and fourth holes (205 and 206) of the button 201 and through the through holes in the locking pin 203 to form one or more tensioning member loops.

The baseplate 110 is preferably oblong in shape with at least two openings (e.g. 111, 112), but preferably four openings (e.g. 111, 112, 113, 114). In the preferred embodiment, the tensioning member 102 loops (or passes) three times through the two center openings 111 and 112 of the baseplate 110 and two times through the transverse opening 109 to form the tensioning member loops 124 and 125. In another embodiment, the tensioning member 102 loops four times through the two center openings 111 and 112 and three times through the transverse opening 109 of the locking pin 103 to form the tensioning member loops 124, 125 and 126. In both the above embodiments, the tensioning member 102 further passes through the first opening 104 and the second opening 106 of the button 101 and up through the one or more pinch points 119 of the locking pin 103 as shown in FIG. 1. The two outer openings 113 and 114 of the baseplate 110 can be used for additional and optional operations such as housing "passing sutures" used to pull the baseplate 110 through a hole drilled in bone.

In an embodiment, the one or more pinch points 119 create locking (pinching) force to the tension stored in the tensioning member loop 124, 125 and 126 of the assembly 100 as discussed above. Moreover, the indentations 116 of the locking pin 103 along with the individual openings 104 and 106 for each loose tensioning member end 121 in this embodiment help rotationally constrain the button-suture assembly 100 so that the tensioning member 102 does not twist (excepting the twisting of the tensioning member 102 along its long axis) while tensioning or during use.

Figure 2:
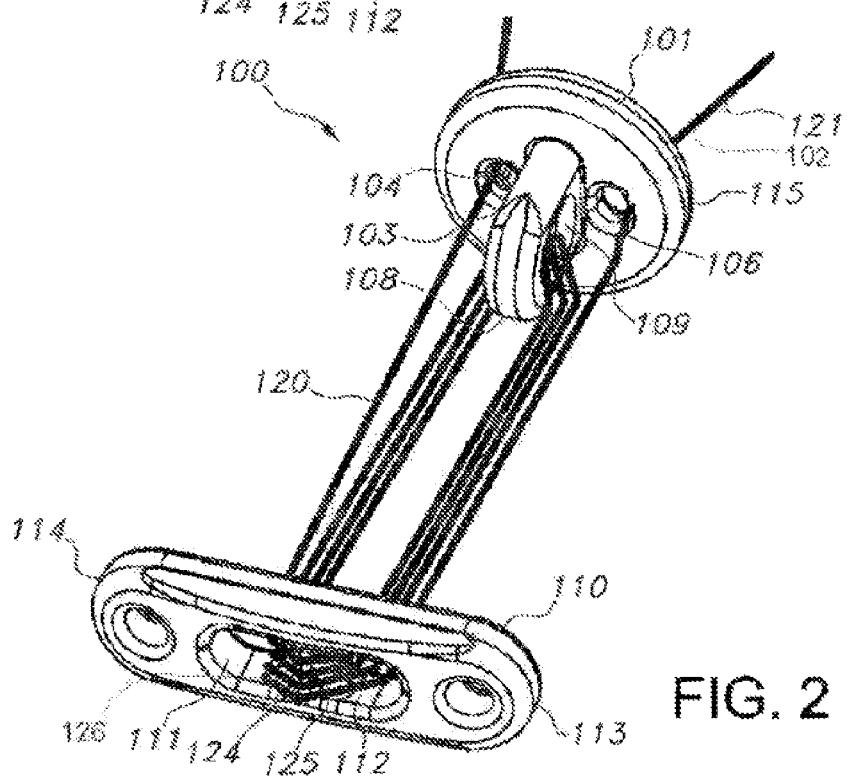
FIG. 2 depicts a perspective view of an embodiment of the button-suture assembly.
Figure 3:
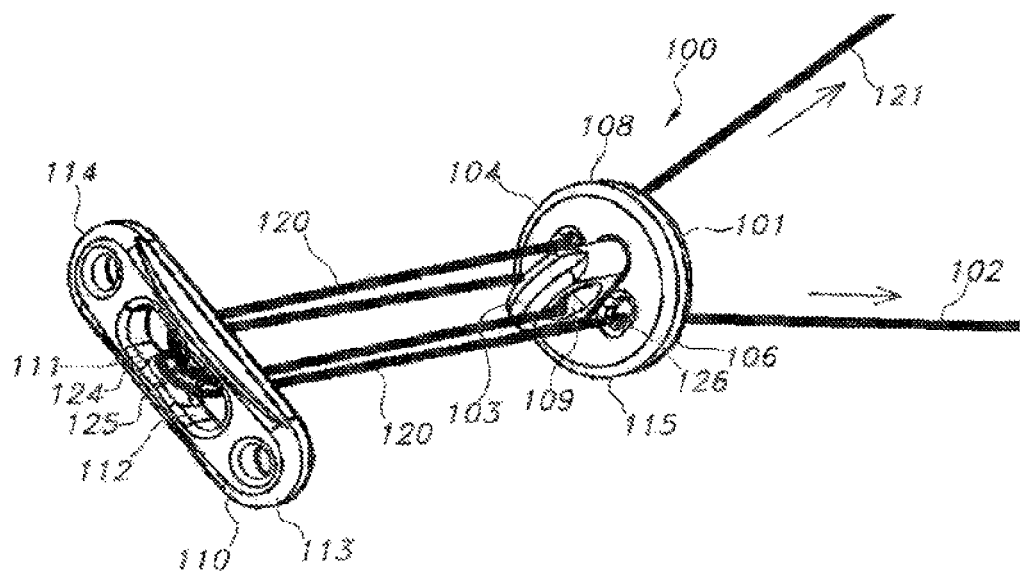
FIG. 3 depicts another perspective view of an embodiment of the button-suture assembly.
Figure 4:
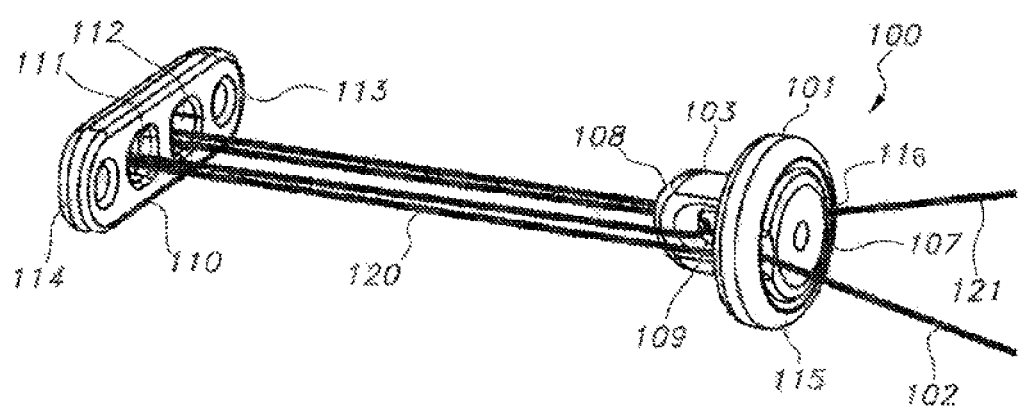
FIG. 4 depicts yet another perspective view of an embodiment of the button-suture assembly.

The button suture assembly 100 also contemplates the tensioning member 102 looping or passing through the two center openings 111 and 112 of the baseplate 110 and transverse opening 109 of the locking pin 103 various numbers of time. For instance, as shown in FIG. 3, the tensioning member 102 may loop through the two center openings 111 and 112 of the baseplate 110 twice and through the transverse opening 109 of the locking pin 103 once to form the tensioning member loops 124 and 125. Alternatively, the tensioning members may loop through the two center openings 111 and 112 of the baseplate 110 four times and through the transverse opening 109 of the locking pin 103 three times to form the tensioning member loops 124, 125, and 126 as depicted in FIG. 2. The increased number of tensioning member loops (124, 125 and 126) through the baseplate 110 provides increased stability of the button suture assembly 100 and better procedure outcomes.

The described embodiments allow decreasing the length of tensioning member loops 124, 125 and 126 between the baseplate 110 and the button 101 and the locking pin 103 sub-assembly (also referred to in the description as suspension device 115) by means of pulling on loose tensioning member ends 121. The pulling force applied on loose tensioning member ends 121 results in a movement of the tensioning member loops 124 and 125 relative to the baseplate 110, but preferably not moving the tensioning member loops 124, 125 and 126 relative to the locking pin 103.

At a state when the proximal surface of the baseplate 110 and the distal surface of the button 101 make contact with bone surfaces, applying tension (pulling force) in the proximal direction to the loose tensioning member ends 121, causes the locking pin 103 to translate proximally relative to the button 101. The proximal translation is for a small amount of length that is preferably greater than zero but less than 1 mm and more preferably less than 0.50 mm and most preferably less than 0.25 mm. This proximal translation of the locking pin 103 is caused by the fact that the spacing between the loose tensioning member ends 121 as they enter the button 101 (through the openings 104 and 106), is smaller than the spacing allowed by the proximal end 107 of the locking pin 103 as the loose tensioning member ends 121 exit the suspension device 115 (best seen in an embodiment in FIG. 7A). Since the loose tensioning member ends 121 are pulled in proximal direction during the tensioning step, this difference in spacing causes the tensioning member ends 121 to exert a proximally-directed force on the locking pin 103. The step of pulling the loose tensioning member ends 121 as described above creates a tension in the tensioning member loops (e.g., 124, 125, 126). This step is referred to in this description as the "tensioning step" or "tensioning". As discussed above, it is desirable to prevent the tensioning member loops (124, 125, 126) from slacking or relaxing when the pulling force or tension is released (or ceases to exist) to precisely secure the bones or tissue fragments by the assembly. The disclosed invention provides for a (retaining) mechanism to utilize the tension created during the "tensioning step" in the tensioning member loops (124, 125, 126) and the double tensioning member loop 120 to automatically lock the assembly and prevent retraction of the tensioning member 102 in the distal direction with respect to the suspension device 115.

When the tension applied to the tensioning member ends is released or ceases to exist, the tension stored in the tensioning member loops 124, 125 and 126 results in compressive forces exerted on the bony anatomy by the baseplate 110 and the button 101. The tension stored in the tensioning member loops 124, 125 and 126 further causes the locking pin 103 to translate distally with respect to the button 101 thereby bottoming out on and applying pressure to the tensioning member 102 around one or more pinch points 119 shown for example in FIG. 4. Consequent to the releasing of pressure or pulling force on the tensioning member 102, the assembly is automatically locked and resists any further lengthening of the tensioning member loops 124, 125 and 126 (best seen in an embodiment in FIG. 7B). This step of automatically restraining the proximal movement of the tensioning member 102 due to pressure applied at the one or more pinch points 119 is hereinafter referred to as the "locking step" or "locking".

It should be understood that the amount by which the locking pin 103 moves proximally during the tensioning step and the amount by which the locking pin 103 moves distally when the tension on the loose tensioning member ends 121 is released or ceases to exist (during the locking step) are contemplated to impact the amount by which the assembly will "spring back" or relax as discussed above. Therefore, the lower the proximal displacement of the locking pin 103 required to pull the tensioning member 102 through the suspension device 115 the lower the relaxation the assembly will experience during the locking step.

Furthermore, it is contemplated that the size of elongate central opening 105 in the button 101 could prevent the tensioning member loop 124, 125 and 126 from passing through. This arrangement results in a stable assembly where the locking pin 103 cannot be completely withdrawn from the button 101 after assembly and while the tensioning member loops 124, 125 and 126 passes through transverse opening 109 within it. Furthermore, due to each of the loose tensioning member ends 121 passing through their own dedicated openings 104 and 106 in the button 101, the assembly functions in a predictable manner where the tensioning member ends 121 and the locking pin 103 translate through the button 101 in preferably one direction (generally proximal or distal).

In the procedure utilizing the preferred embodiment of the button-suture assembly 100, a hole is drilled through bones, tensioning members 102 are passed through the hole and fixated on the distal side of the hole. The bones are then pulled closer together and tensioning members are "tensioned" or tightened by pulling on the loose tensioning member ends 121 in the proximal direction allowing a precise adjustment of the button-suture assembly 100 as necessary. Once the tensioning step is complete, the button-suture assembly 100 automatically locks in place and holds the tension with preferably minimal relaxation or slip-back.

Figure 7B:
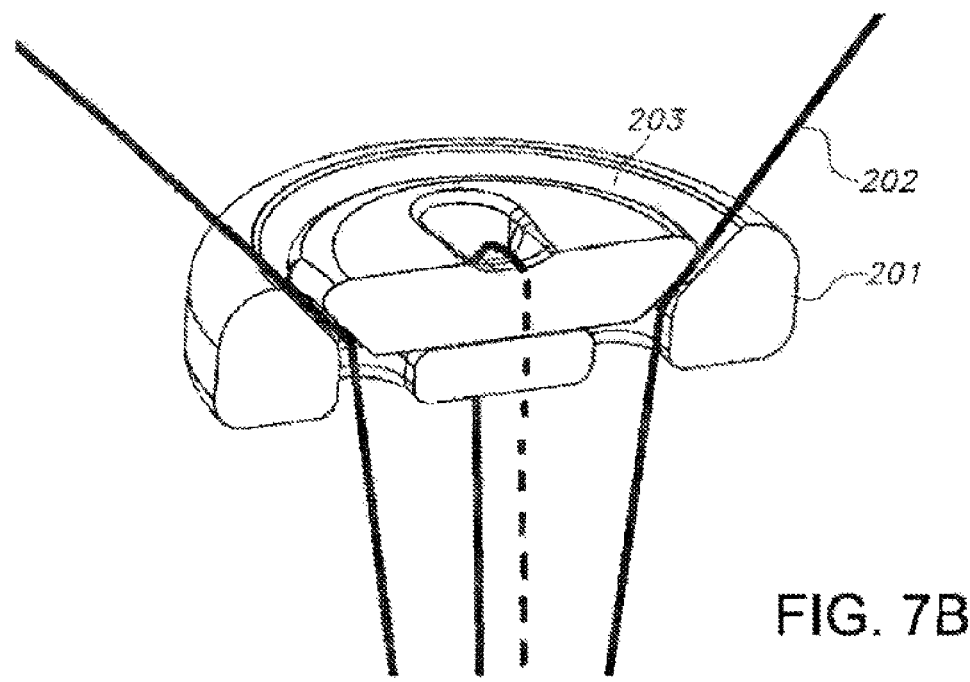
Figure 8A:
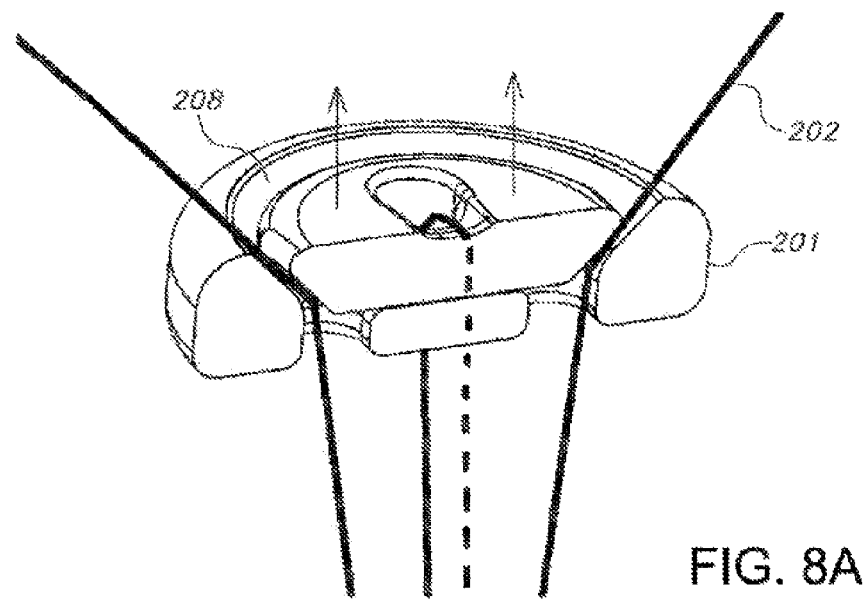
FIGS. 8A-8B depict the unlocking mechanism of the suspension device. Individually.
Figure 8B:
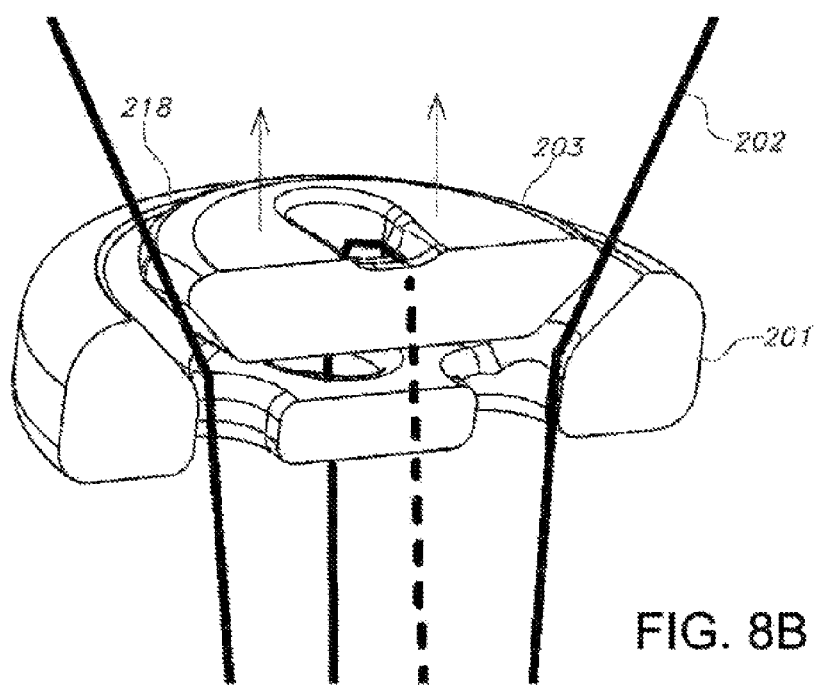

In an embodiment, the button-suture assembly 100 also allows for unlocking and loosening the assembly if re-tensioning or repositioning is desired by means of applying tension in the proximal direction to the locking pin and causing it to translate proximally as shown in FIG. 8A & FIG. 8B. As shown, an upward force or tension is applied on the locking pin (e.g., 203) to pull the locking pin in proximal direction beyond the proximal surface 218 of the button 201. This step of loosening the assembly by applying tension (or pulling) in the proximal direction to the locking pin (103 or 203) is referred to as "unlocking step" or "unlocking". The tensioning member 202 (or 102) experiences a slack thereby allowing the tensioning member loops (e.g., 124, 125) to increase in length in the absence of any tension or pulling force on the tensioning member ends (121). More specifically, after a hole is drilled through the surface of a bone or other member, the double tensioning member loop 120 is passed through the indentions 116 of the suspension device 115 and tensioned by pulling on the ends 121 of the double tensioning member loop 120 in the proximal direction, and locking the button-suture assembly 100 in place once the tensioning force is released as discussed above. As shown in FIG. 7B, when no pull is applied to the tension member ends 121, the tension in the double tensioning member loop 120 (or the tensioning member loop 124, 125, 126) section prevents the loop from lengthening via tensioning member 102 being locked in the one or more pinch points 119. Alternatively, pulling on the locking pin 103 unlocks the suspension device 115. In this state, the double tensioning member loop 120 can be lengthened by pulling on the button 101, as described above and shown in FIGS. 8A-8B.

Figure 14:
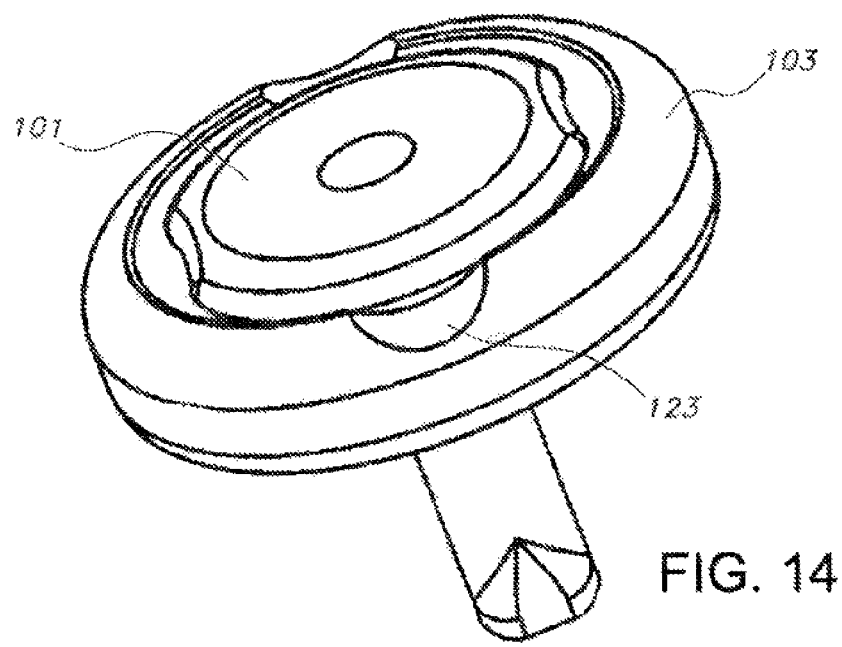
FIG. 14 depicts an embodiment of the button with tool access cuts.
Figure 15:
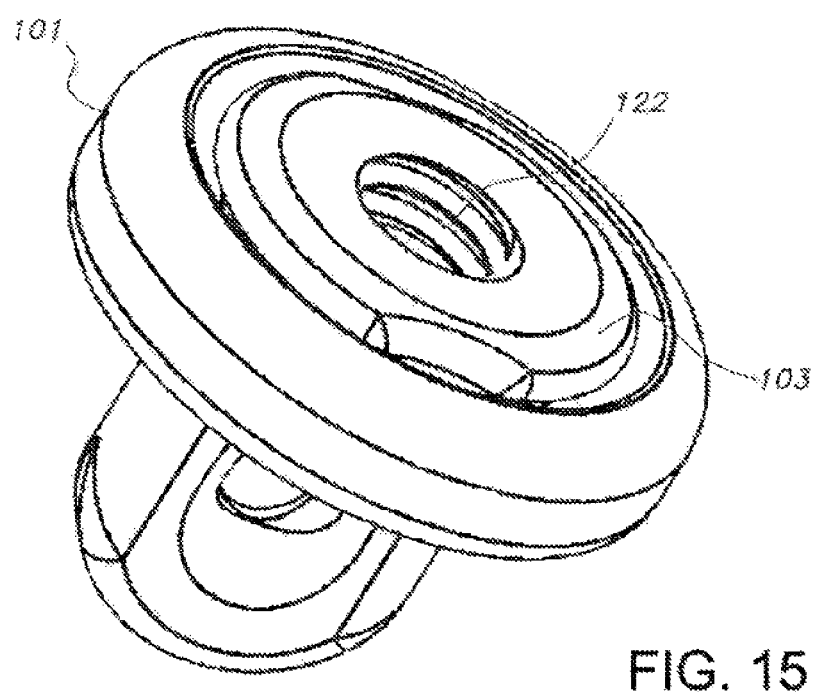
FIG. 15 depicts an embodiment of a threaded locking pin.

The suspension device 115 can be unlocked in any way that separates the locking pin 103 from the button 101. These mechanisms include, but are not limited to, prying the locking pin 103 with a pick-like instrument. The locking pin 103 can have specialized features for pulling it up with either general or specialized surgical instruments. In the preferred embodiment, the locking pin 103 is long enough that it can be pushed back through the suspension device 115 from a distal end of the locking pin 103. The button-suture assembly 100 also contemplates various additional features to aid in the unlocking of the suspension device 115, such as an internal threaded region 122 in the locking pin 103 and one or more tool access cuts 123 on the exterior proximal surface of the button 101 (as shown in FIGS. 14 and 15).

FIG. 9 and FIG. 10 depict perspective views of another embodiment of the button-suture assembly. As shown and described with reference to FIGS. 7A-7B and FIGS. 8A-8B, the first and second openings mate with the two loose tensioning member ends and the third and fourth openings (205 and 206) of the button 201 coincide with the through holes of the locking pin 203 respectively. The tensioning member 202 passes through the first and second openings (204) of the button 201 and the double tensioning member loop 200 passes through two holes of the baseplate and then through the third and fourth holes (205 and 206) of the button 201 and then through the holes in the locking pin 203 to form one or more tensioning member loops.

Figure 11A:
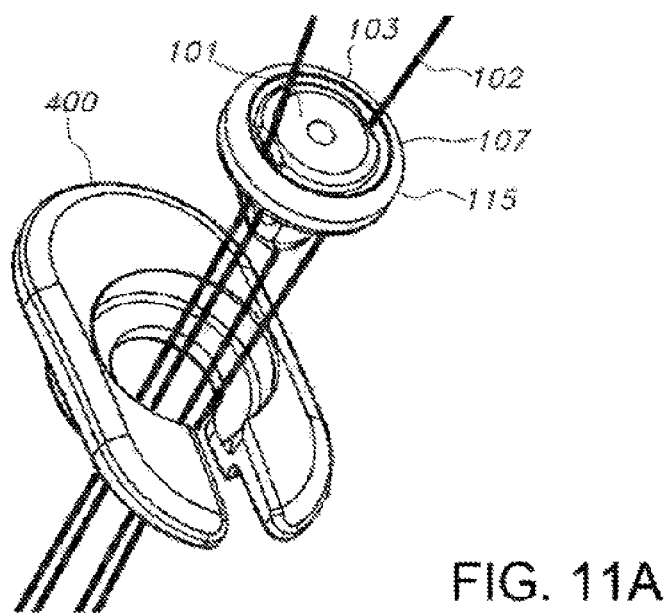
FIGS. 11A-11B depict another embodiment of the button suture assembly.
Figure 11B:
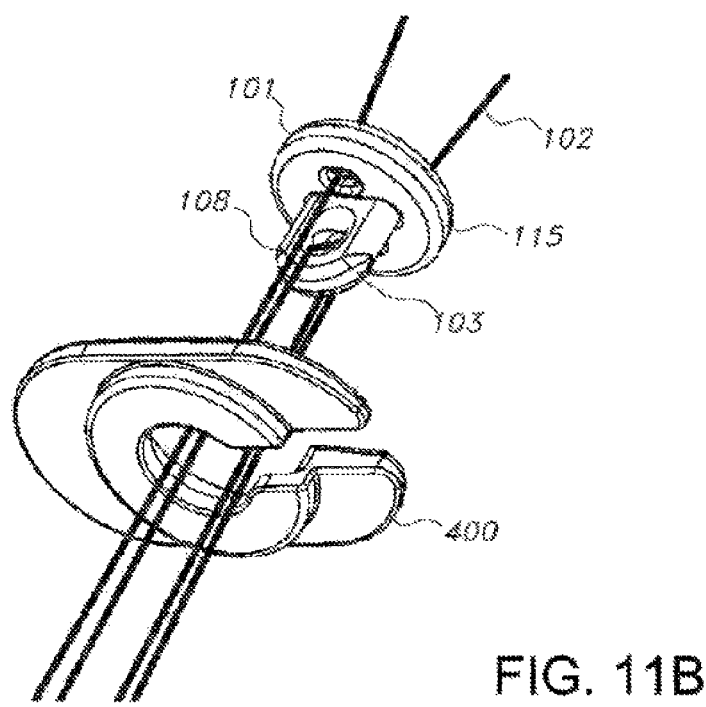

In an embodiment, the button-suture assembly includes a guiding member 400 having a passage to allow the tensioning members 102 to pass through. The cross-sectional dimension of the proximal surface of the guiding member 400 is such that it prevents the suspension device 115 to pass through the passage as shown in perspective views in FIG. 11A and FIG. 11B.

Figure 12A:
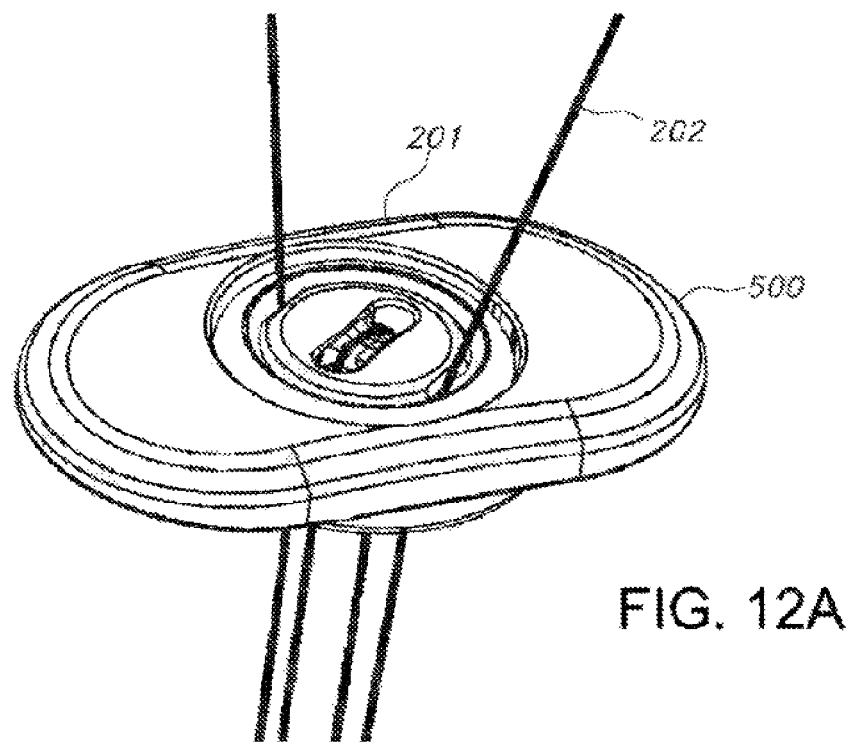
FIGS. 12A-12D depict an embodiment of the button-suture assembly with a footprint extender. Individually.
Figure 12B:
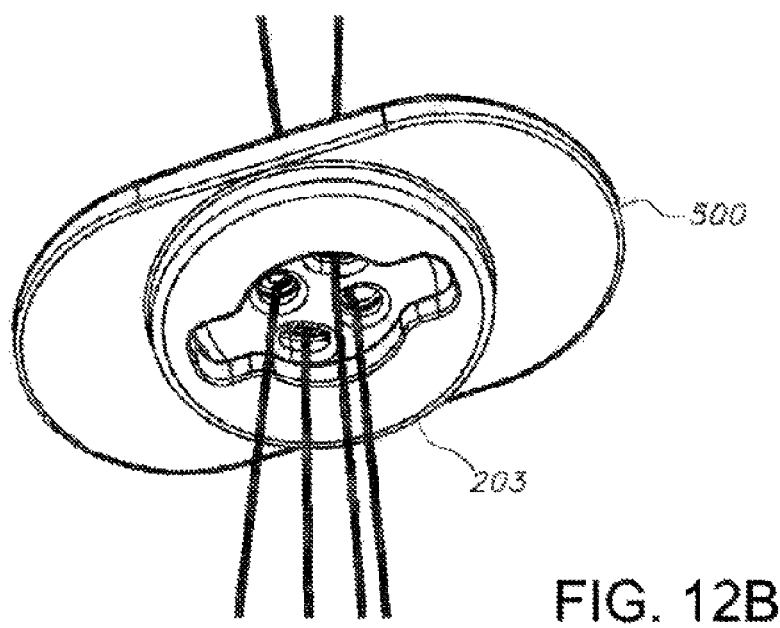
Figure 12C:
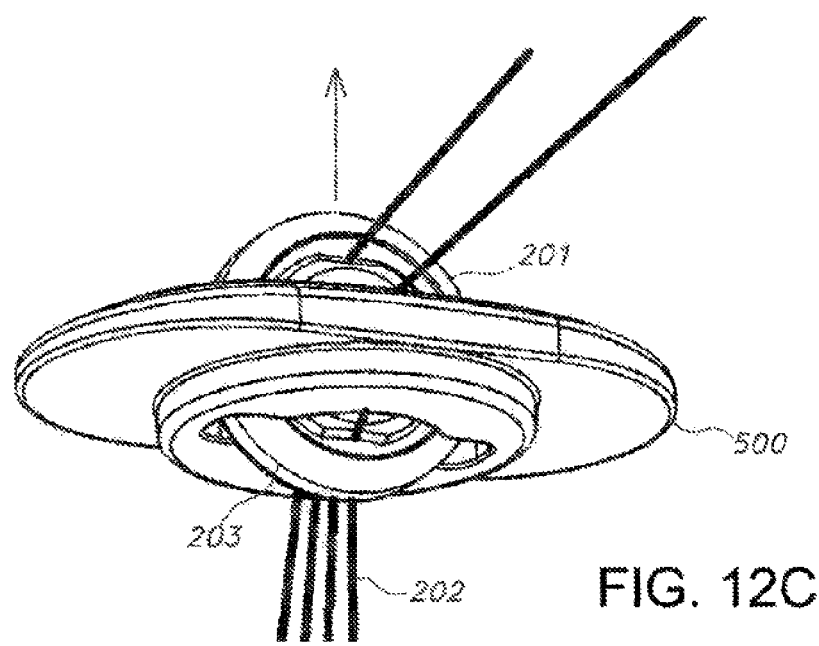
Figure 12D:
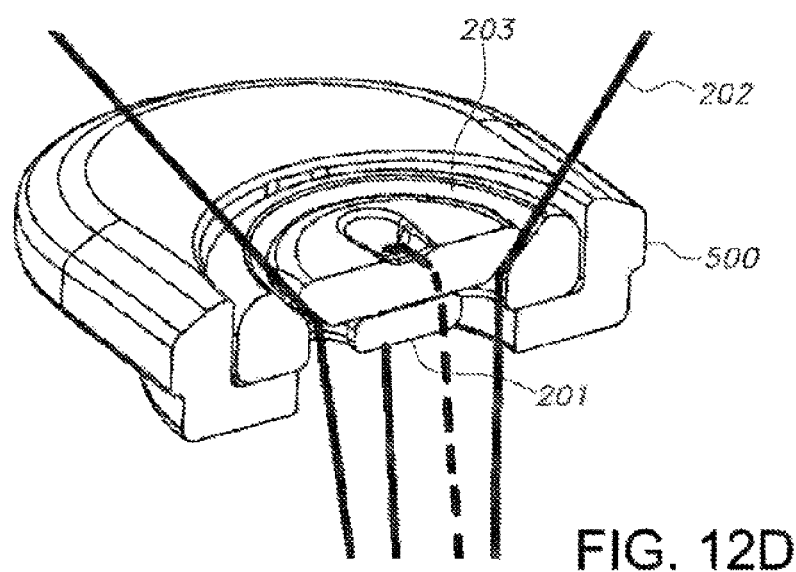

In an embodiment, the button-suture assembly includes a footprint extender 500. FIGS. 12A-12D depict an embodiment of the button-suture assembly with the footprint extender. FIG. 12A and FIG. 12B depict perspective views of the button-suture assembly with footprint extender. FIG. 12C depicts a perspective view of the button 201 being pulled through the footprint extender 500. FIG. 12D depicts a cross-sectional view of the button 201 inside the footprint extender 500.

Figure 13A:
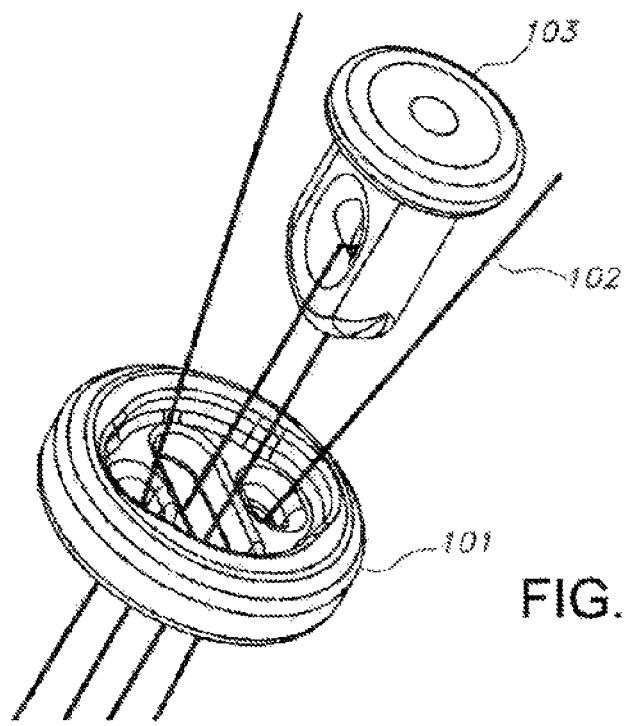
FIGS. 13A-13B depict another embodiment of the button-suture assembly. Individually.
Figure 13B:
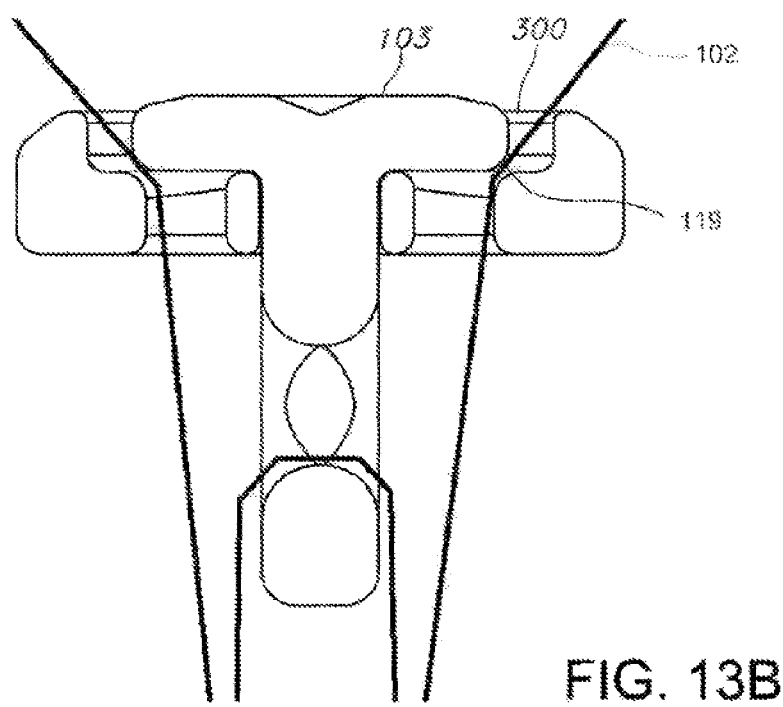

FIG. 13A depicts a perspective view of the button-suture assembly with the locking pin 103 unlocked and completely retracted from the button 101 in the proximal direction as a consequence of the "unlocking step". FIG. 13B depicts a sectional view of the button-suture assembly in a locked configuration. The locking pin 103 mates with the button 300 to create one or more pinch points 119 to restrain or prevent any distal movement of the tensioning member 102.

Figure 16:
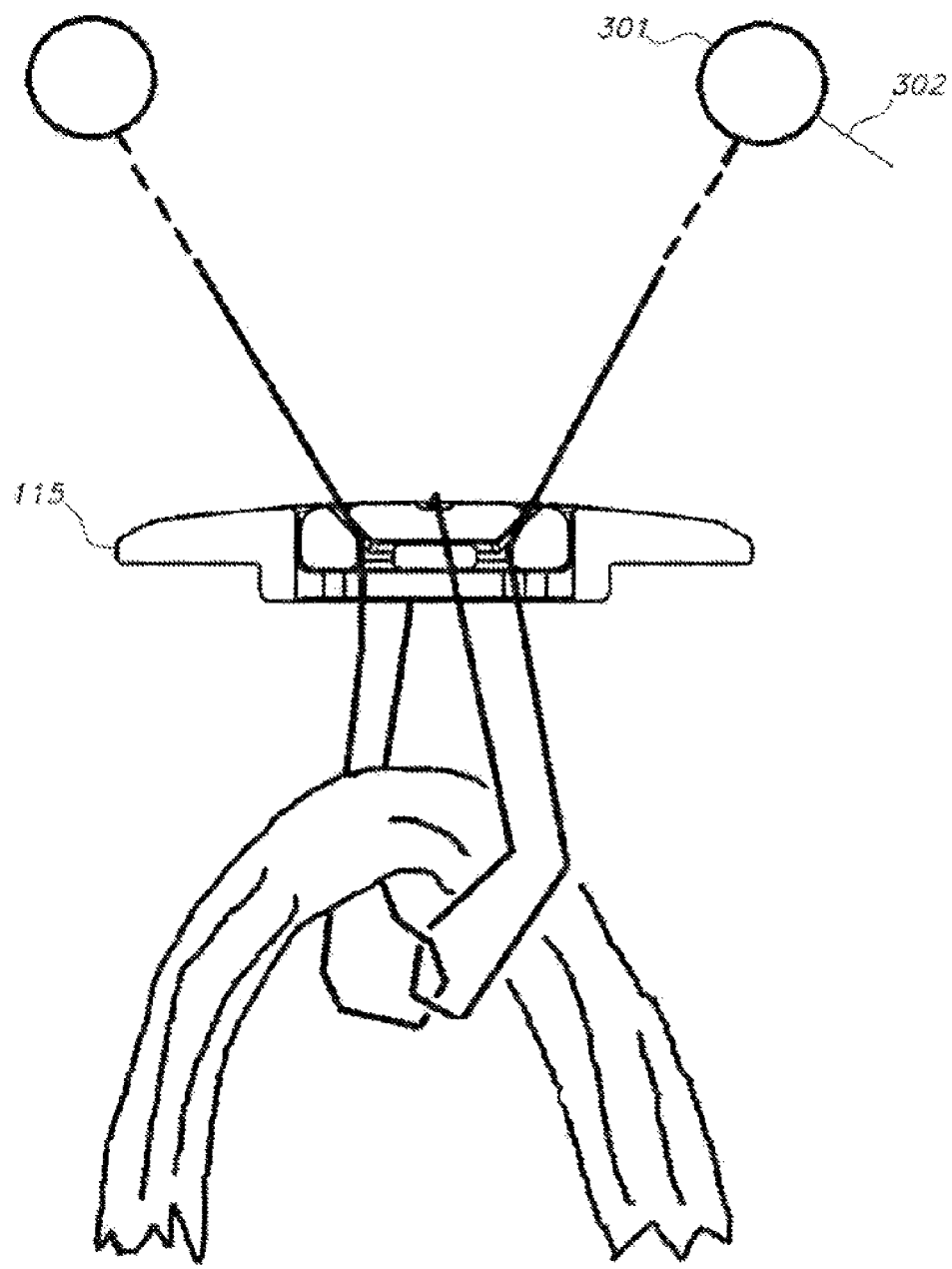
FIG. 16 depicts a top plan view of an embodiment of the button-suture assembly with pull rings.

FIG. 16 depicts a top plan view of an embodiment of the button-suture assembly with pull rings. As shown, the button-suture assembly can include two pull rings 301 to enable easy pulling of the tensioning member 302 fixed or wound on the pull rings 301. During a procedure, the physician may find it easy to pull the tensioning member 302 using pull rings 301 in a proximal direction with respect to the suspension device 115.

Figure 17:
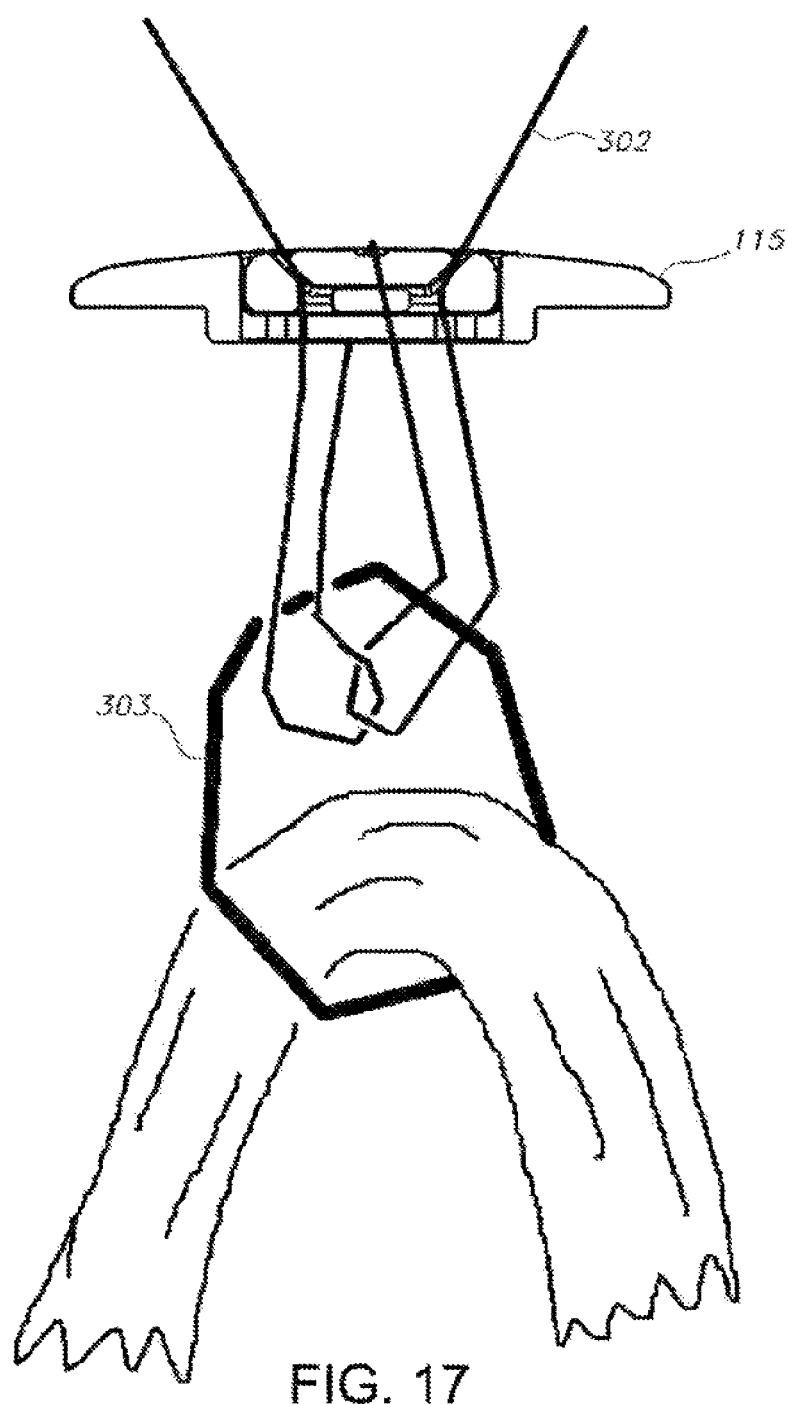
FIG. 17 depicts a top plan view of an embodiment of the button-suture assembly with a continuous loop.

FIG. 17 depicts a top plan view of an embodiment of the button-suture assembly with a continuous loop 303. In an embodiment, the continuous loop 303 loops over the tensioning member 302 may to hold together tissue fragments as shown.

Figure 18:
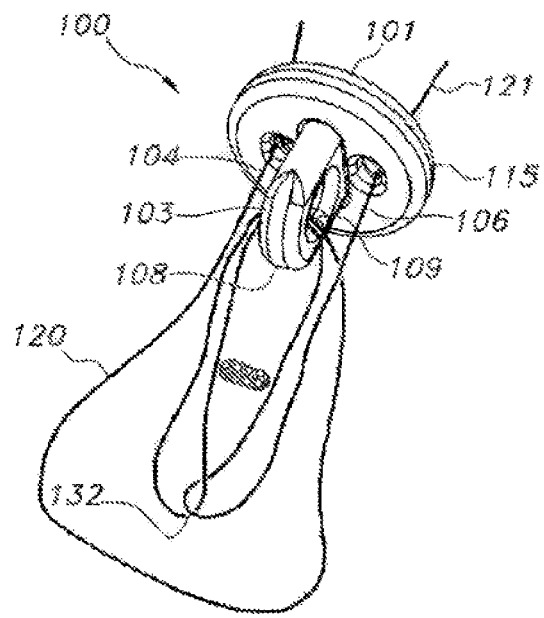
FIG. 18 depicts another perspective view of an embodiment of the button-suture assembly.
Figure 19:
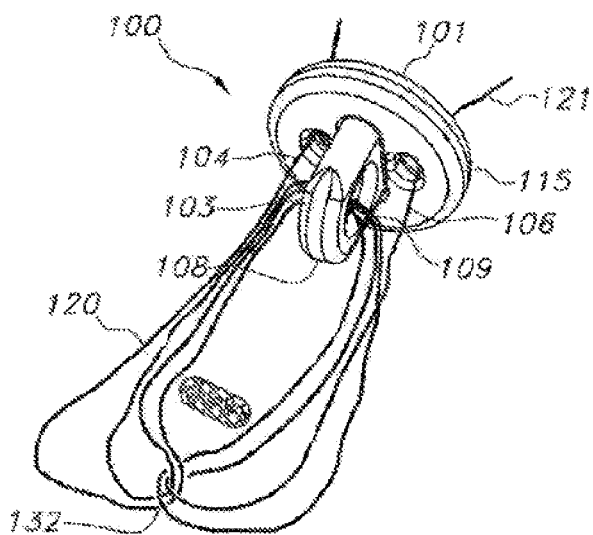
FIG. 19 depicts an embodiment of the button-suture assembly

In an alternate embodiment, a baseplate is not used in the button-suture assembly 100. Instead, the tensioning members loop through each other and through the transverse opening 109 of the locking pin 103 two times to form the tensioning member loops 132, as depicted in FIG. 18, to secure a graft or other members during a procedure. In yet another embodiment, the tensioning members may loop through each other and through transverse opening 109 of the locking pin 103 three times to form the tensioning member loops 132, as depicted in FIG. 19.

Figure 20:
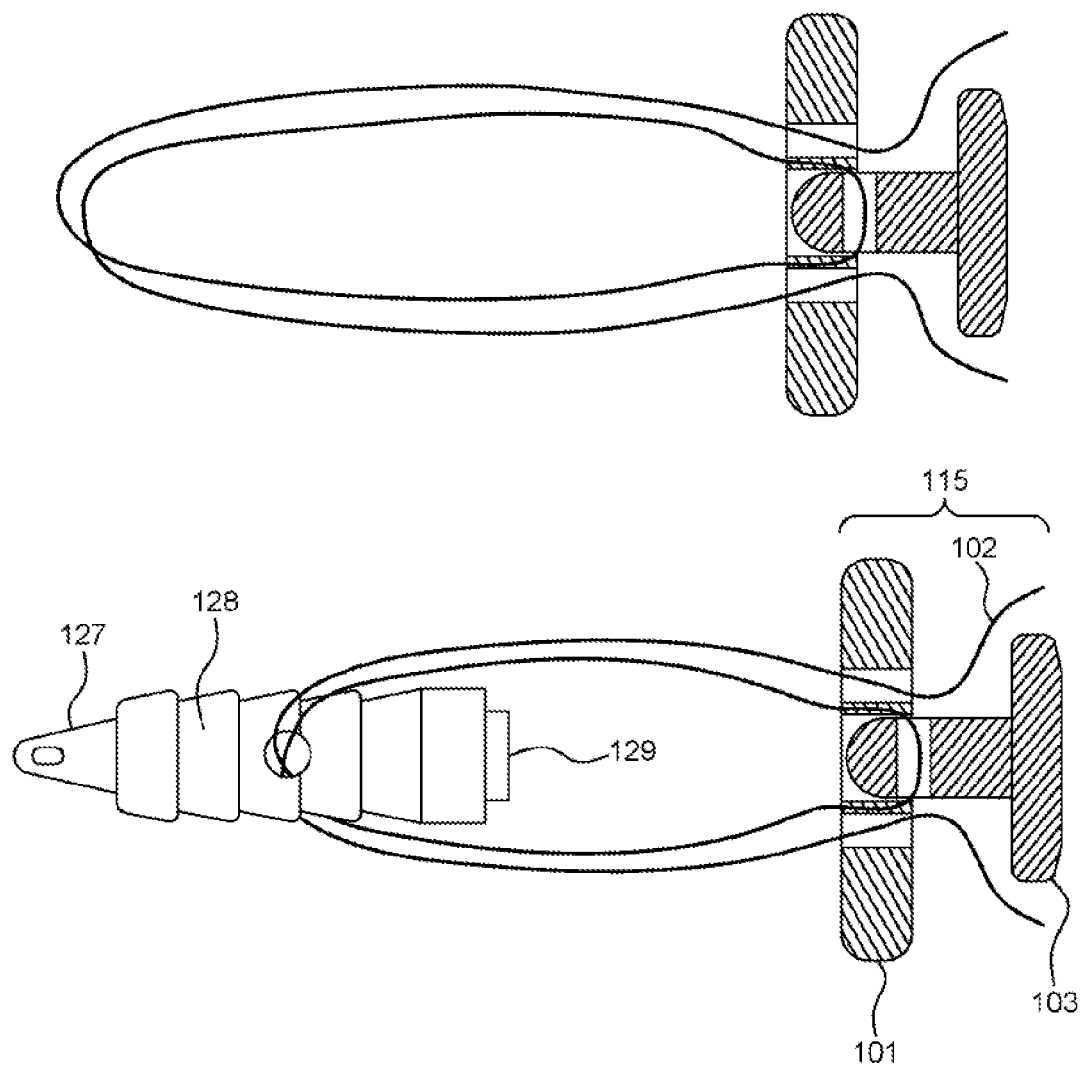
FIG. 20 depicts another embodiment of the button-suture assembly including an anchor.
Figure 24:
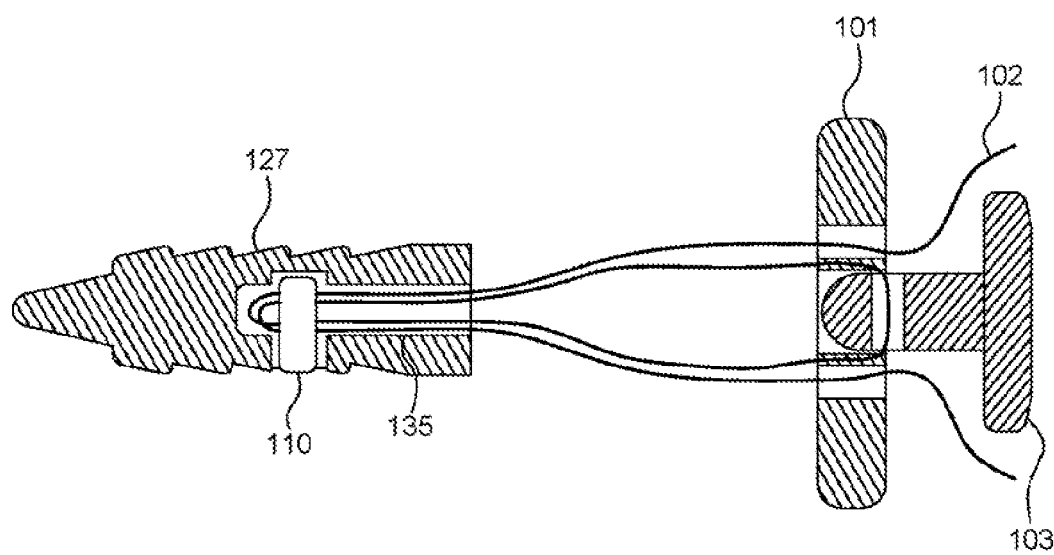
FIG. 24 depicts another embodiment of the button-suture assembly including a baseplate and an anchor.
Figure 29:
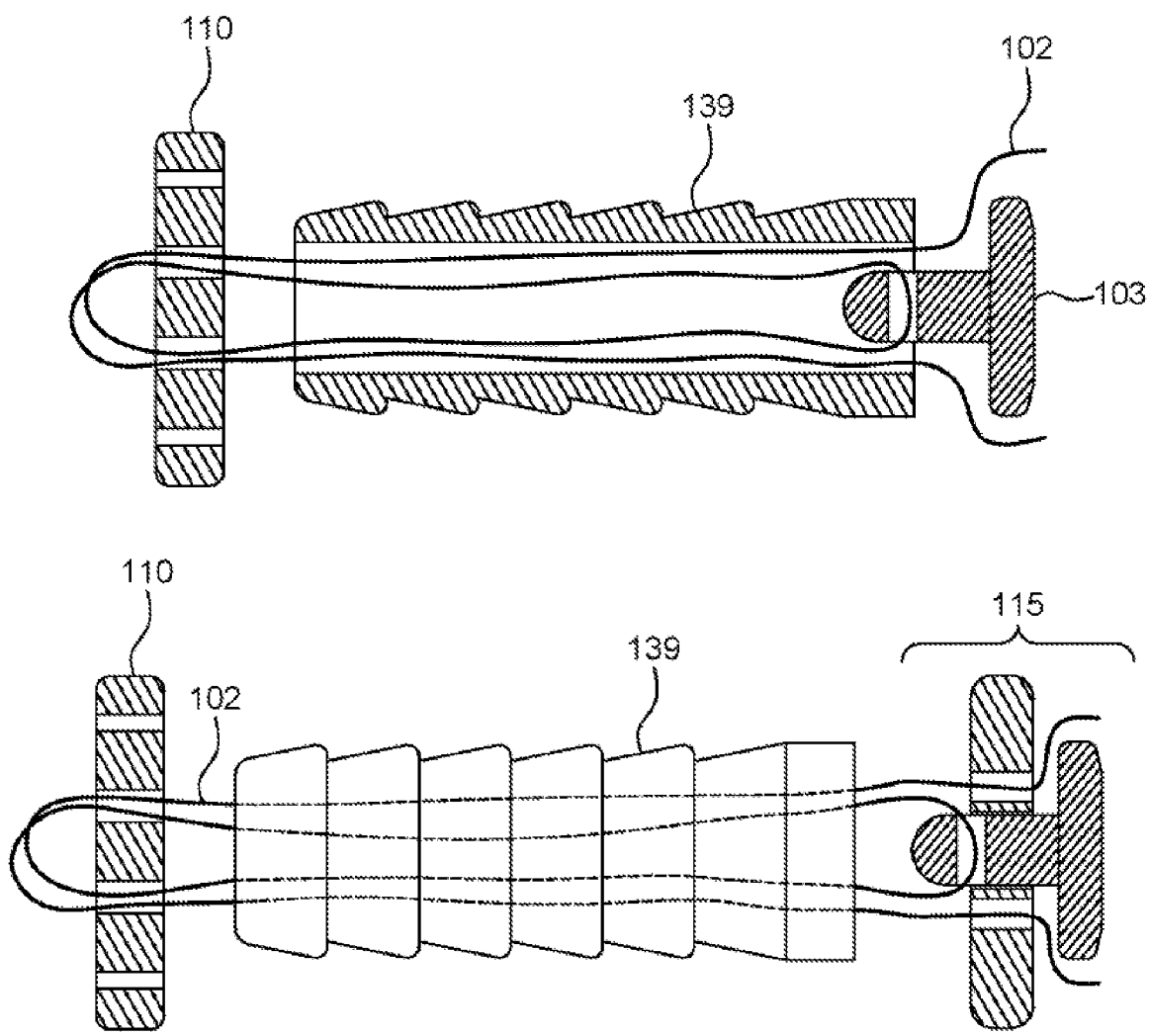
FIG. 29 depicts an embodiment of the button-suture assembly including a headless screw and a baseplate.

In an alternate embodiment, the button-suture assembly 100 can include an anchor 127. In such an embodiment, the tensioning member 102 loops through a center opening of the anchor 127 as shown in FIG. 20 (or screw 139 as shown in FIG. 29), rather than a baseplate 110. The tensioning member 102 then passes through the transverse opening 109 of the locking pin 103 and then through the two outer openings 104 and 106 of the button 101 and up through the pinch points 119 of the locking pin 103, to form one or more tensioning member loops as shown in FIG. 20. The anchor 127 may be a threaded device, such as a screw 139, or can contain a pointed distal tip to assist with insertion of the anchor 127 into the bone during a procedure. The anchor 127 may further be comprised of a hollow interior anchor body 128. Also, the anchor 127 may have a threaded lateral surface. In another embodiment, the anchor 127 may have one or more vertical slots 135 along its length to facilitate the tensioning members 102 to slide down the anchor 127 (as shown in FIG. 24).

Figure 21:
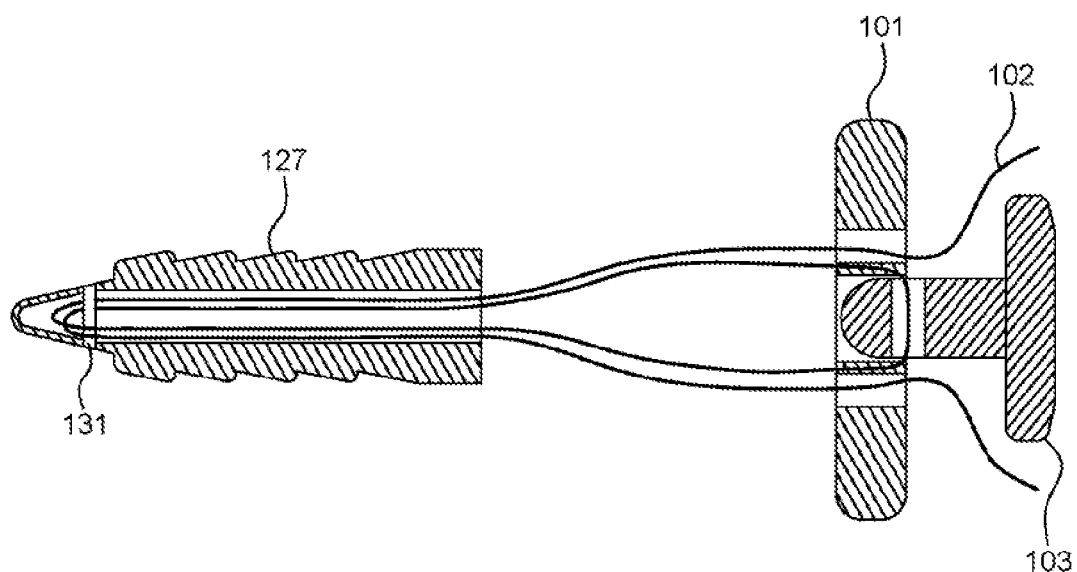
FIG. 21 depicts another embodiment of the button-suture assembly including an anchor.

In an alternate embodiment, the anchor 127 contains an interior horizontal connecting piece or interior horizontal bridge 131 that the tensioning members 102 pass over, as shown in FIG. 21. In this embodiment, the sutures or the tensioning members 102 are inside the anchor 127, instead of a baseplate 110, and tensioned and adjusted in the same manner described above. It is contemplated that the horizontal bridge 131 is an interior keyhole or other shape capable of maintaining the tensioning members 102 inside the anchor 127.

Figure 22:
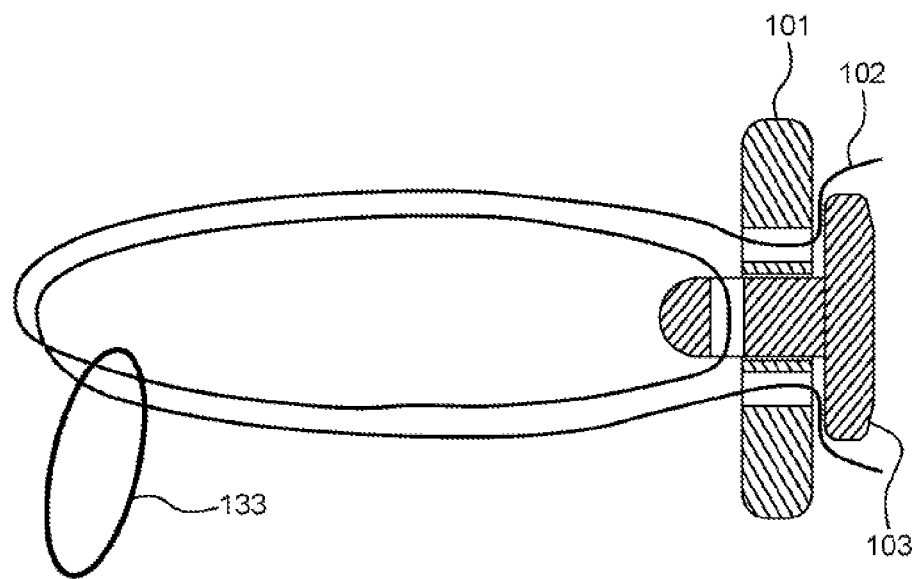
FIG. 22 depicts an embodiment of the button-suture assembly including a secondary fixed loop.

All of the embodiments described herein can include a secondary fixed loop 133 around the tensioning member loops that is similar to a ring around a main adjustable loop and can be made out of any material similar to the (primary) tensioning member 102, as shown in FIG. 22.

Figure 23:
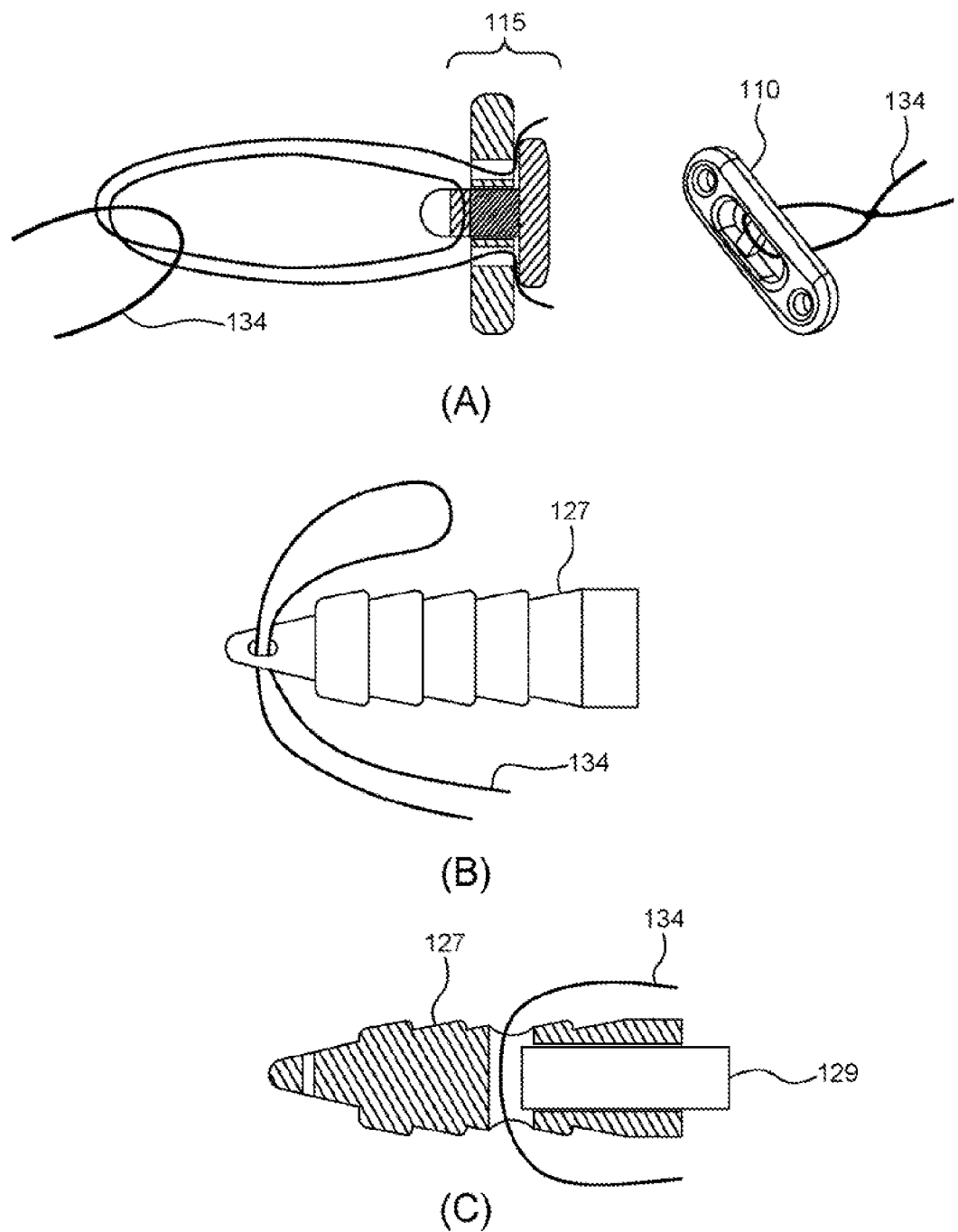
FIG. 23 depicts embodiments of the button-suture assembly including a tape.

In an alternate embodiment, a tape 134 is looped around the tensioning member loops extending from the suspension device 115, as shown in FIG. 23. Tape 134 can also be used to pass through a free baseplate 110 (as shown in FIG. 23A) rather than a fixation baseplate 110. In another embodiment, the tape 134 is also contemplated to go through the anchor 127 (as shown in FIG. 23B) or in between the anchor 127 and a secondary anchor component 129 or screw 139, as shown in FIG. 23C. In this embodiment, the locking happens when the anchor 127 with the tape 134 is driven into the bone and the tape 134 gets locked between the bone and the exterior of the anchor 127. Alternatively, the secondary anchor component 129 locks the tensioning member 102 in or on top of the primary anchor 127. The locking on the other side happens when the tensioning members 102 of the suspension loop that the tape 134 wraps around is pulled to reach adequate tension of the repair. The tension in this embodiment can be adjusted by adjusting the anchor 127 or the locking pin 103 in the suspension device 115. Additionally, the tension can be adjusted by changing the position of the secondary anchor component 129. Once the anchor 127 is inserted in the bone, the tension of the construct can be manipulated by pulling on the tensioning member 102 to lock the assembly and soft tissue or other body member down.

The tension member 102 can be any member capable of passing through the anchor slot or applicable component, including, but not limited to, a fiber, a suture, a tape, a tissue graft, a polymer or other materials listed herein.

In an embodiment, the anchor 127 is driven into the bone, and the tension member 102 is urged into the anchor body 128 as shown in FIG. 24. The tensioning member 102 is tensioned so that the locking pin 103 can impinge and lock the tensioning member 102 on the baseplate 110. The tension can be adjusted by adjusting the tensioning members 102 around the locking pin 103 and/or adjusting the anchor 127. In an alternate embodiment, the anchor 127 has one or more vertical slots 135 to slide the tensioning member 102 and a cavity to insert the baseplate 110, as shown in FIG. 24. The vertical slot 135 of the anchor 127 contains a ridge that secures the baseplate 110 within the anchor 127 and prevents it from sliding inside the anchor 127. As the physician pulls on the tensioning members 102 sliding through the vertical slot 135, the baseplate 110 catches on the ridge and remains secure inside the anchor 127 as the repair procedure is performed. The vertical slots 135 can be a groove cut along the length of the anchor 127 or the screw 139 that may include a floor.

Figure 25:
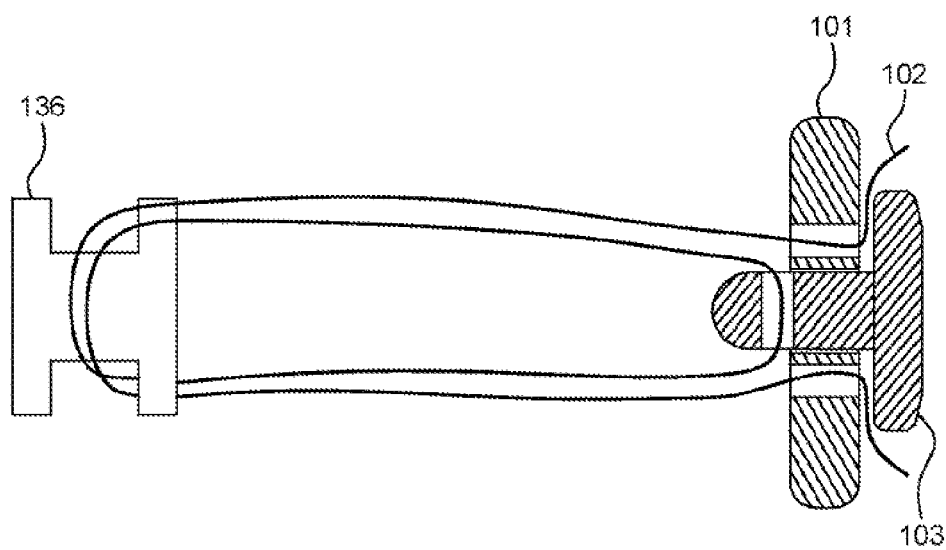
FIG. 25 depicts an embodiment of the button-suture assembly including a baseplate having indentations.

In an alternate embodiment, the button-suture assembly includes a plate 136 with at least one indentation, rather than a standard baseplate 110, particularly when an oblong hole in the body or body member is not preferred, as shown in FIG. 25. The plate 136 can be any suitable shape and contain a plurality of indentations, as long as it is capable of acting as a bridge on the bone or tunnel which the tensioning member 102 loop around. In this embodiment, the plate 136 can also be attached to a fracture or similar plate or prosthesis, with the suspension device 115 locking into the future plate or prosthesis. Procedures like these currently use stainless steel wires but use of the plate 136 and tensioning member 102 allows for a stronger tensioned construct or assembly.

The locking features described herein can also be designed in a way where the locking pin 103 can lock in the fracture plate of prosthesis or an extension to an existing plate which has mating surface to the locking pin 103 and may have an extension to wrap the tensioning member 102 loops on the plate, plate extension or may be used with plate similar to plate 136 or baseplate 110.

Figure 26:
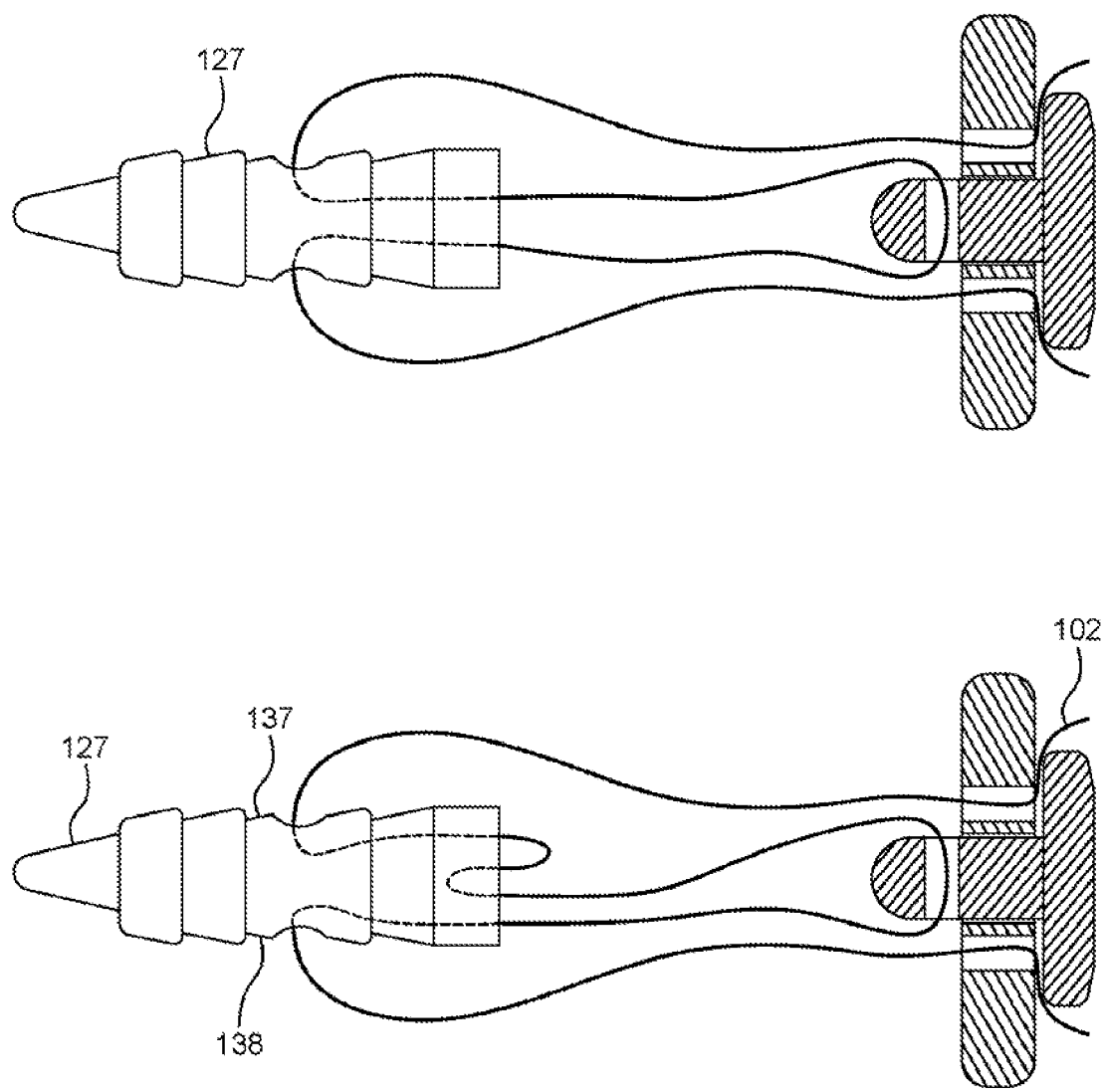
FIG. 26 depicts embodiments of the button-suture assembly including an anchor having one or more keyholes.

In an alternate embodiment, tensioning members 102 loop through a keyhole or slotted opening in the locking pin 103 and through vertical slots 135 or an interior keyhole of an anchor 127, as shown in FIG. 26. The tensioning members 102 pass through the holes in the anchor body 128 and the locking pin 103. The tensioning happens when the tensioning members 102 are pulled and the locking pin 103 collapses in the button 101.

In an embodiment, the tensioning members 102 form an extra loop that may or may not be used to augment the repair with a graft (as shown in FIG. 26). As the tensioning members 102 are pulled, the extra loop formed by the tensioning members 102 passing through the anchor body 128 shortens. In this embodiment, the anchor 127 is typically implanted prior to tensioning using the suspension device 115.

Figure 27:
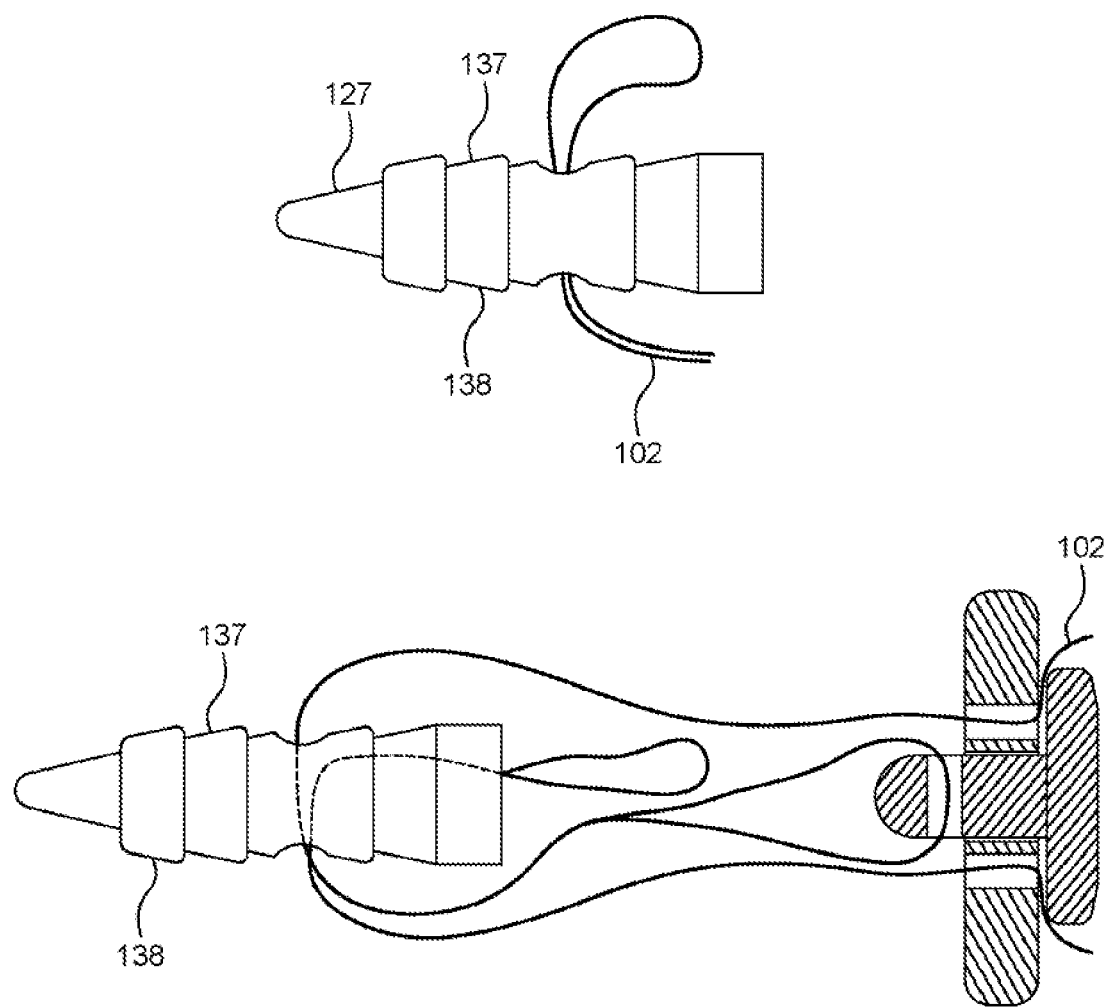
FIG. 27 depicts an embodiment of the button-suture assembly including an anchor having a center hole.

In an alternate embodiment, a first tensioning member 102 passes through a hole in a first side 137 of the anchor 127 through the interior of the anchor body 128, as shown in FIG. 27. The first tensioning member 102 has a loop that can be used to tension the repair. On a second side 138 of the anchor body 128, a second tensioning member 102 goes in a first hole and out a second hole. The second tensioning member 102 also has a loop that is connected to the locking pin 103. The first tensioning member 102 is pulled to adjust the tension of the repair, and once appropriate tension is reached, the second tensioning member 102 is pulled to move the locking pin 103 distally into the button 101 to lock the entire construct. The tension can again be attuned by making adjustments on the anchor 127 side or on the side of the locking pin 103. The tensioning member 102 may pass continually through the sides of the anchor 127 or loop through and be constrained on one side by a knot or other mechanism.

The anchor 127 and the secondary anchor component 129 can be constructed by using any material typically used in the industry, including, but not limited to, PEEK, polymer, metal, fiber material, polymer composite. The anchor 127 may or may not have vertical slots 135, keyholes or a groove/slit/cut on the side of the anchor body 128 of the anchor 127. In addition, the tensioning members 102 can be any member capable of passing through the anchor slot or applicable component and providing tension, including, but not limited to, a fiber, a suture, a tape, a polymer, or PEEK.

Figure 28:
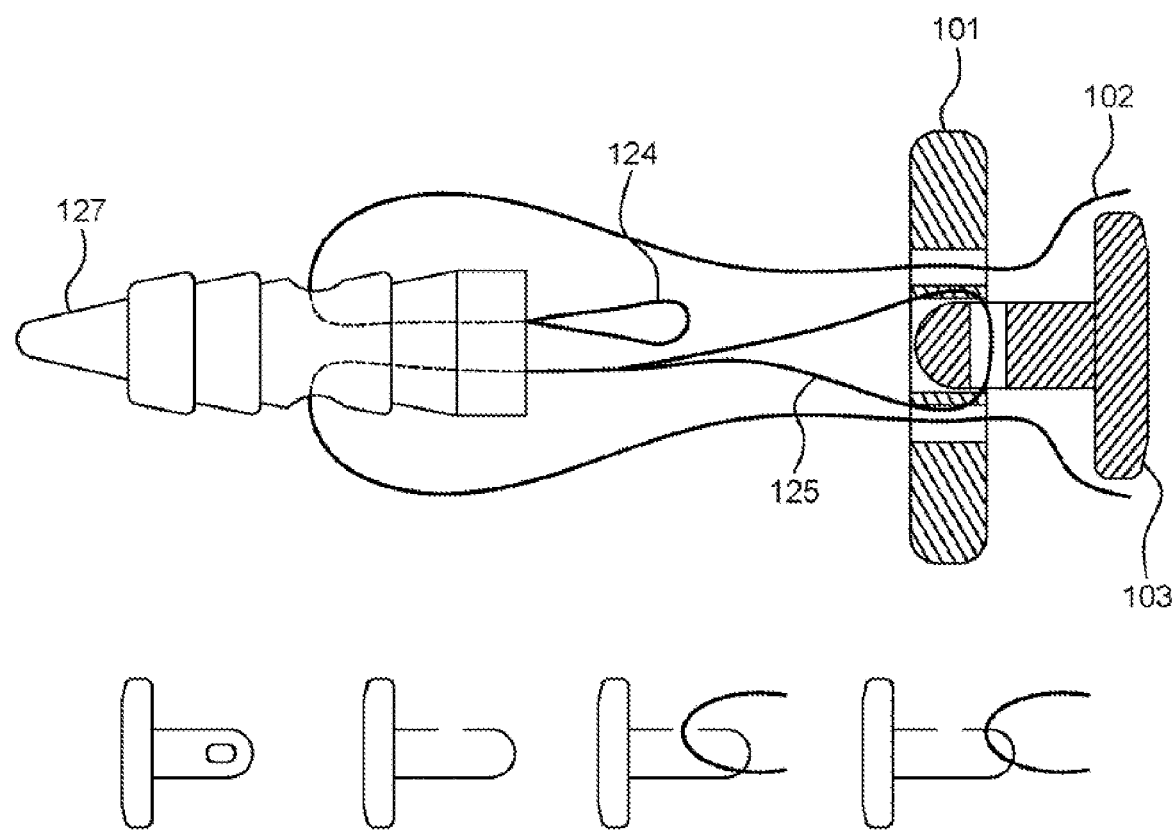
FIG. 28 depicts another embodiment of the button-suture assembly including an anchor.

In yet another embodiment, the tensioning member 102 forms a first loop 124 that exits from the interior of the anchor 127 and a second loop 125 that also exits the interior of the anchor 127 but is attached to the locking pin 103 or can be docked in the locking pin 103 through the (transverse) opening 109 in the locking pin 103, as shown in FIG. 28. The anchor 127 may have a slot or channel on the exterior surface to facilitate sliding of the tensioning members (tensioning member) and loop. Preferably, the first tensioning member 102 is initially pulled to shorten the first tensioning member loop 124, then the second tensioning member 102 is pulled to shorten the second tensioning member loop 125, which will pull the locking pin 103 and lock the construct. It is preferred that the second tensioning member 125 loops through a slot rather than a keyhole in the locking pin 103, so that when the second tensioning member 125 is in the slot of the locking pin 103, it pulls the locking pin 103 down and locks the construct.

For example, when utilizing this embodiment in a surgical procedure implanting the device inside the bone, an anchor 127 with vertical slots 135 or an interior keyhole is driven into the bone. A graft is made around the first collapsing tensioning member loop 124 to lock the graft in the interior of the anchor body 128 or besides the anchor 127, while pulling on the second tensioning member loop 125 to tension or cram the construct. In this embodiment, if the tensioning members 102 are exterior to the anchor 127 rather than passed through the interior keyhole, the tensioning members 102 don't get jammed in between the bone and anchor 127.

In an alternate embodiment, the button-suture assembly includes a screw 139. The suspension device 115 is tensioned to abut the screw 139 or other similar anchoring devices, as shown in FIG. 29. The screw 139 may or may not have a head. In case of a headless screw 139, the fixation of tensioning members 102 occurs where the headless screw 139 and suspension device 115 meet, with the suspension device 115 collapsing in the screw 139 and locking the tensioning members 102. This embodiment may include, but does not require, the baseplate 110. Without the baseplate 110, the tensioning member 102 loops and/or the tensioning member 102 is passed through the screw 139, which can be passed through the bone or other body member. In an embodiment, the button 101 of the suspension device 115 may not be required. Without the button 101, the tensioning member 102 passes through the holes of the screw 139 towards the base of the screw 139, and the locking pin 103 collapses and locks the tensioning member 102 between the holes of the screw 139, body of the screw 139 and the locking pin 103.

For example, when a fracture and soft tissue need to be repaired at the same location, a headless screw 139 is inserted, and the baseplate 110 is passed through the interior channel of the headless screw 139. The baseplate 110 can be flipped to engage the bone, or the tensioning member 102 can be passed over a bridging plate. Subsequently, the tensioning members 102 are pulled to lock the construct. The locking pin 103 may have a through hole or a slot to dock the tensioning member 102.

Figure 30:
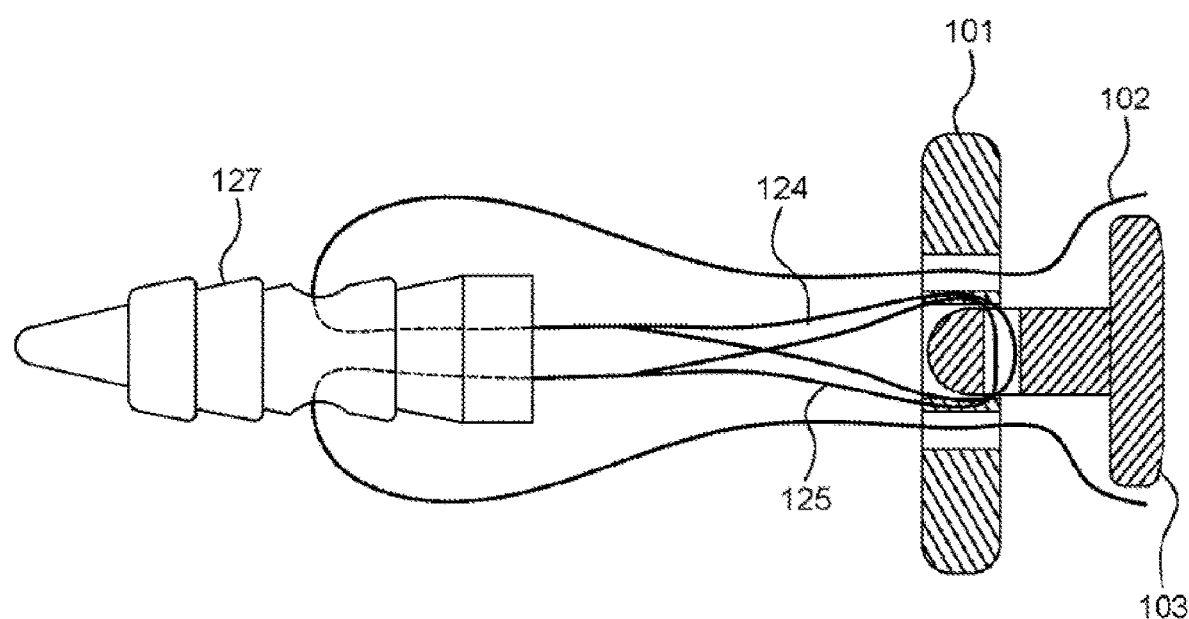
FIG. 30 depicts an embodiment of the button-suture assembly including an anchor and multiple tensioning member loops.

In an alternate embodiment, the tensioning member 102 passes through the vertical slots 135 or the interior keyhole of the anchor 127 once, and twice through the transverse opening 109 of the locking pin 103 to form the tensioning member loops 124 and 125, as shown in FIG. 30. The two tensioning members 102 with loops docked in the locking pin 103 are on the exterior surface of the anchor 127 and can slide through the opening, slot or hole of the anchor 127. Pulling on the free tensioning member 102 will cause both loops to pull on the locking pin 103 and lock the device/ assembly in place. The anchor 127 having vertical slots 135 on the exterior may assist with sliding of the tensioning member 102 and locking of the construct or the assembly.

Embodiments of a suspension device (e.g., 115) for orthopedic stabilization are disclosed. In an embodiment, the suspension device 115 includes a button (e.g., 101) having a first opening (e.g., 104), a second opening (e.g., 106) and a center opening (e.g., 105). The suspension device 115 further includes a locking pin (e.g., 103) having a proximal member and a distal member. The center opening of the button is configured to receive the distal member of the locking pin to form a mating arrangement configured to allow a proximal movement of a tensioning member (e.g., 102) passing through the first opening and the second opening when a pulling force is applied to the loose ends (e.g., 121) of the tensioning member in a proximal direction with respect to the button and prevent a distal movement of the tensioning member when the pulling force applied to the loose ends of the tensioning member ceases to exist.

In an embodiment, the locking pin translates in a proximal direction relative to the button when the pulling force is applied to the two tensioning member ends towards the proximal direction during a tensioning step. Furthermore, the locking pin translates in a distal direction relative to the button (during a locking step) when the pulling force ceases to exist subsequent to the applying of the pulling force to the two tensioning member ends towards the proximal direction. In an embodiment, the locking pin has two indentations located on the proximal member of the locking pin disposed along the first opening and the second opening respectively to create two corresponding passages between the locking pin and an interior surface of the circumference of the button for the tensioning member to pass through.

As described above, the mating arrangement between the locking pin and the button creates one or more pinch points (e.g., 119) in the two passages when the pulling force ceases to exist after the applying of the pulling force to the tensioning member. The proximal member of the locking pin has a cross-sectional dimension greater than the center opening and wherein the distal end of the locking pin has a cross-sectional dimension similar to the center opening. The tensioning member can be manufactured from a material selected from a group comprising of polymer filaments, metallic filaments, organic filaments, carbon fiber and carbon nanotubes. In an embodiment, the tensioning member has a length that lies in the range of around 300 mm to around 1000 mm.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation. Additionally, it should be understood that various embodiments of the suspension device described herein contain optional features that can be individually or together applied to any other embodiment shown or contemplated here to be mixed and matched with the features of that device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

I claim:

1. An orthopedic stabilization device comprising:
a suspension device comprising a button and a locking pin, the button having a central opening, first and second lateral openings positioned on opposite sides of the central opening, and a receiving surface configured to mate with the locking pin, the locking pin having a proximal end, a distal end, a distal member, and a mating surface configured to mate with the receiving surface of the button, the locking pin configured to mate with the button such that the distal member extends through the central opening in the button;
a tensioning member having a first tensioning member end passing through the first lateral opening and a second tensioning member end passing through the second lateral opening, the first and second tensioning member ends disposed outwardly towards a proximal direction of the button; and
an anchor configured for insertion into bone, the anchor having an outer surface configured for purchase in bone and a center opening;
wherein the tensioning member forms one or more tensioning member loops by passing through a transverse opening in the distal member of the locking pin and the center opening of the anchor; and
wherein the first and second tensioning member ends pass through the first and second lateral openings, respectively, immediately before passing between the receiving surface of the button and the mating surface of the locking pin.

2. The orthopedic stabilization device of claim 1, wherein mating surface of the locking pin further comprises two indentations located on the proximal end of the locking pin and configured for positioning proximate the first lateral opening and the second lateral opening respectively to create two corresponding passages between the mating surface of the locking pin and of the receiving surface of the button for the tensioning member to pass through.

3. The orthopedic stabilization device of claim 2, wherein the passages allow a proximal movement of tensioning member when a pulling force is applied to the tensioning member ends towards the proximal direction.

4. The orthopedic stabilization device of claim 3, wherein the passages prevent distal movement of tensioning member when the pulling force ceases to exist subsequent to the applying of the pulling force to the tensioning member ends.

5. The orthopedic stabilization device of claim 1, wherein the tensioning member corresponds to one of: a coreless suture, a suture with a jacket and a central core, and a tape.

6. The orthopedic stabilization device of claim 1, wherein an inner circumference of the locking pin is threaded.

7. The orthopedic stabilization device of claim 1, wherein the center opening comprises a hollow interior of the anchor.

8. The orthopedic stabilization device of claim 7, wherein the at least one tensioning member loop is maintained inside the hollow interior.

9. The orthopedic stabilization device of claim 7, wherein the anchor further comprises an interior horizontal connecting piece within the hollow interior.

10. The orthopedic stabilization device of claim 7, wherein the at least one tensioning member loops passes over the interior horizontal connecting piece, and the interior horizontal connecting piece maintains the tensioning member loop inside the hollow interior.

11. The orthopedic stabilization device of claim 1, wherein the anchor includes a pointed distal tip to assist with insertion of the anchor into bone.

12. The orthopedic stabilization device of claim 1, wherein the anchor comprises a headless screw, and the center opening comprises a hollow interior of the anchor.

* * * * *